(12) United States Patent
Badie et al.

(10) Patent No.: US 11,369,305 B2
(45) Date of Patent: *Jun. 28, 2022

(54) HEART FAILURE PROGRESSION MONITORING BASED ON LV CONDUCTION PATTERN AND MORPHOLOGY TRENDS

(71) Applicant: Pacesetter, Inc., Sylmar, CA (US)

(72) Inventors: Nima Badie, Berkeley, CA (US); Jan O. Mangual-Soto, Rho (IT); Luke C. McSpadden, Los Angeles, CA (US); Louis-Philippe Richer, Montreal (CA); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/740,553

(22) Filed: Jan. 13, 2020

(65) Prior Publication Data

US 2020/0146577 A1 May 14, 2020

Related U.S. Application Data

(63) Continuation of application No. 15/963,836, filed on Apr. 26, 2018, now Pat. No. 10,582,866.

(51) Int. Cl.
*A61B 5/00* (2006.01)
*A61B 5/316* (2021.01)
(Continued)

(52) U.S. Cl.
CPC ............ *A61B 5/316* (2021.01); *A61B 5/0022* (2013.01); *A61B 5/287* (2021.01); *A61B 5/35* (2021.01); *A61B 5/686* (2013.01); *A61B 5/7264* (2013.01); *A61B 5/352* (2021.01); *A61N 1/3704* (2013.01); *A61N 1/3925* (2013.01)

(58) Field of Classification Search
CPC ....... A61B 5/316; A61B 5/367; A61B 5/4842; A61B 5/7275; A61B 5/35; A61B 5/287; A61B 5/686; A61B 5/0022; A61B 5/7264; A61B 5/352; A61N 1/3925; A61N 1/3704;
(Continued)

(56) References Cited

U.S. PATENT DOCUMENTS 9,669,218 B2   6/2017 Libbus et al.
2012/0190957 A1 * 7/2012 Gill .................... A61B 5/4842
                                              600/374

* cited by examiner

*Primary Examiner* — Scott M. Getzow
(74) *Attorney, Agent, or Firm* — The Small Patent Law Group LLC; Dean D. Small

(57) ABSTRACT

Computer implemented methods, devices and systems for monitoring a trend in heart failure (HF) progression are provided. The method comprises sensing left ventricular (LV) activation events at multiple LV sensing sites along a multi-electrode LV lead. The activation events are generated in response to an intrinsic or paced ventricular event. The method implements program instructions on one or more processors for automatically determining a conduction pattern (CP) across the LV sensing sites based on the LV activation events, identifying morphologies (MP) for cardiac signals associated with the LV activation events and repeating the sensing, determining and identifying operations, at select intervals, to build a CP collection and an MP collection. The method calculates an HF trend based on the CP collection and MP collection and classifies a patient condition based on the HF trend to form an HF assessment.

20 Claims, 12 Drawing Sheets

(51) Int. Cl.
*A61B 5/35* (2021.01)
*A61B 5/287* (2021.01)
*A61N 1/39* (2006.01)
*A61N 1/37* (2006.01)
*A61B 5/352* (2021.01)

(58) Field of Classification Search
CPC .. A61N 1/36842; A61N 1/3702; G16H 50/30; G16H 50/20
See application file for complete search history.

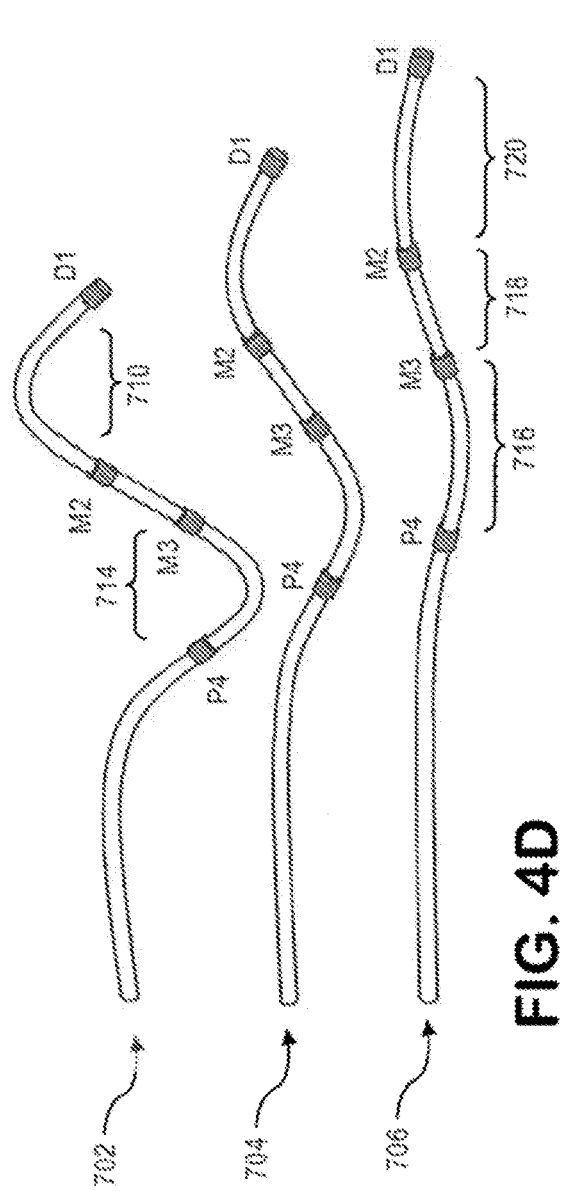
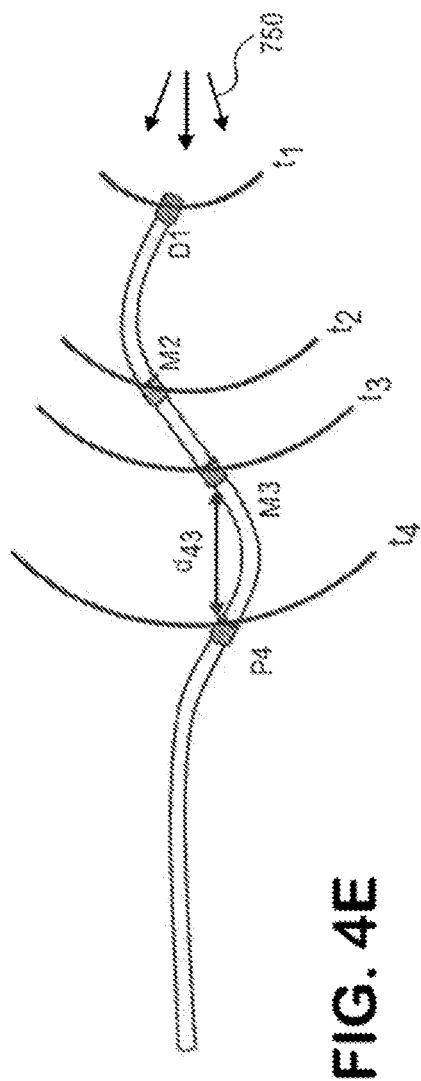
FIG. 4D
FIG. 4E

HEART FAILURE PROGRESSION MONITORING BASED ON LV CONDUCTION PATTERN AND MORPHOLOGY TRENDS

REFERENCE TO RELATED APPLICATIONS

The present application is a continuation application of, and claims priority to, U.S. application Ser. No. 15/963,836, Titled "HEART FAILURE PROGRESSION MONITORING BASED ON LV CONDUCTION PATTERN AND MORPHOLOGY TRENDS" which was filed on Apr. 26, 2018, the complete subject matter of which is expressly incorporated herein by reference in its entirety.

BACKGROUND

Embodiments herein relate to tracking trends in left ventricular conduction patterns and morphology in connection with monitoring heart failure progression.

Implantable medical devices (IMD) provide various types of electrical stimulation, such as in connection with delivering pacing therapy to one or more select chambers of the heart. An IMD may provide both unipolar and bipolar pacing and/or sensing configurations. In the unipolar configuration, the pacing pulses are applied (or responses are sensed) between an electrode carried by the lead and a case of the pulse generator or a coil electrode of another lead within the heart. In the bipolar configuration, the pacing pulses are applied (or responses are sensed) between a pair of electrodes carried by the same lead. IMD's may implement single-chamber or dual-chamber functionality. Recently, IMDs have been introduced that stimulate multiple sites in the same chamber, termed multisite stimulation systems or multi-purpose pacing systems.

Recently, multi-point pacing (MPP) technology has enabled pacing at multiple left ventricular (LV) sites to improve synchrony in cardiac resynchronization therapy (CRT) patients.

However, over time, at least some CRT patients experience a progression of heart failure disease. Today, heart failure disease progression in CRT patients is generally only monitored in a limited manner, such as during in clinic follow-up visits. During an in clinic visit, echocardiography signals are collected to measure a patient's hemodynamics and/or electrocardiography (ECG) signals are collected to measure the patient's electrical synchrony. In clinic visits provide a single time point snapshot of a patient's cardiovascular status. In clinic visits are infrequent and in some instances, may be performed only after a heart failure disease has progressed to a significant level requiring a patient to be hospitalized. Current systems for monitoring heart failure (HF) disease progression do not afford daily trends in the disease progression.

SUMMARY

In accordance with embodiments herein, a computer implemented method for monitoring a trend in heart failure (HF) progression is provided. The method comprises sensing left ventricular (LV) activation events at multiple LV sensing sites along a multi-electrode LV lead. The activation events are generated in response to an intrinsic or paced ventricular event. The method implements program instructions on one or more processors for automatically determining a conduction pattern (CP) across the LV sensing sites based on the LV activation events, identifying morphologies (MP) for cardiac signals associated with the LV activation events and repeating the sensing, determining and identifying operations, at select intervals, to build a CP collection and an MP collection. The method calculates an HF trend based on the CP collection and MP collection and classifies a patient condition based on the HF trend to form an HF assessment.

Optionally, the calculating the HF trend may comprise calculating a CP-based trend indicator by applying an AT metric to the CP collection and may comprise calculating an MP-based trend indicator by applying an MP metric to the MP collection. The applying the AT metric may comprise applying at least one of a dyssynchrony metric, conduction nonuniformity metric, conduction velocity metric, fastest conduction pathway metric or chronotropic incompetence metric. The applying the MP metric may comprise applying at least one of an electrical synchrony metric, electrically viable local tissue metric, pacing depolarization integral metric, slope based electrical excited ability metric or template matching score metric. The applying the MP metric may comprise applying the MP metric in connection with interelectrode differences between the morphologies associated with different LV sensing sites.

Optionally, the method may compare the CP-based and MP-based trend indicators to corresponding thresholds. The method may classify the patient condition to form the HF assessment based on the comparing. The calculating the HF trend may comprises calculating a CP-based trend indicator and an MP-based trend indicator. The classifying may comprise comparing the CP-based and MP-based trend indicators to corresponding thresholds to classify the patient condition as one of improved, deteriorated or no change. The sensing, determining and identifying operations may be performed by an implantable medical device, while at least a portion of the calculating and classifying operations are performed by at least one of an external device and a remote server. The sensing, determining, identifying, calculating and classifying operations may be performed by an implantable medical device. The method may further comprising transmitting the HF assessment from the implantable medical device to at least one of an external device and a remote server.

In accordance with embodiments herein, a computer implemented method is provided. The computer implemented method comprises monitoring a trend in heart failure (HF) progression in connection with left ventricular (LV) activation events sensed over a select interval, at multiple LV sensing sites along a multi-electrode LV lead. There the activation events are generated in response to an intrinsic or paced ventricular event. The method implements program instructions on one or more processors for automatically, obtains a conduction pattern (CP) collection of conduction patterns across the LV sensing sites, and a morphology (MP) collection of MPs for cardiac signals associated with the LV activation events. The method calculates an HF trend based on the CP collection and MP collection and classifies a patient condition based on the HF trend to form an HF assessment.

Optionally, the calculating the HF trend may comprise automatically calculating, at a local external device and/or a remote server a CP-based trend indicator by applying an activation time (AT) metric to the CP collection and an MP-based trend indicator by applying an MP metric to the MP collection. The applying the AT metric may comprise applying at least one of a dyssynchrony metric, conduction nonuniformity metric, conduction velocity metric, fastest conduction pathway metric or chronotropic incompetence metric. The applying the MP metric may comprise applying at least one of an electrical synchrony metric, electrically viable local tissue metric, pacing depolarization integral metric, slope based electrical excited ability metric or template matching score metric.

Optionally, the obtaining the CP collection and MP collection may comprise at least one of i) accessing memory of an external device or remote server that stores the CP collection and MP collection, ii) receiving the CP collection and MP collection over a wireless communications link between an implantable medical device and a local external device, or iii) receiving the CP collection and MP collection at a remote server over a network connection. The method may sense the LV activation events at the multiple LV sensing sites along the multi-electrode LV lead. The method may determine the conduction pattern across the LV sensing sites based on the LV activation events. The method may identify MPs for cardiac signals associated with the LV activation events and may repeat the sensing, determining and identifying operations, at select intervals, to build the CP collection and the MP collection.

In accordance with embodiments herein, a system for monitoring a trend in heart failure (HF) progression is provided. The system comprises a multi-electrode LV lead to sense left ventricular (LV) activation events at multiple LV sensing sites along the multi-electrode LV lead. The activation events are generated in response to an intrinsic or paced ventricular event. Memory stores program instructions. One or more processors that, when executing the program instructions, are configured to automatically: determine a conduction pattern (CP) across the LV sensing sites based on the LV activation events, identify morphologies (MP) for cardiac signals associated with the LV activation events, repeat the sensing, determining and identifying operations, at select intervals, to build a CP collection and an MP collection, calculate an HF trend based on the CP collection and MP collection and classify a patient condition based on the HF trend to form an HF assessment.

Optionally, the one or more processors may be configured to calculate the HF trend by calculating a CP-based trend indicator by applying an activation time (AT) metric to the CP collection. The one or more processors may be configured to calculate the HF trend by calculating an MP-based trend indicator by applying an MP metric to the MP collection and calculating the HF trend based on the CP-based and MP-based trend indicators. The one or more processors may be configured to calculate the HF trend by comparing current and historic CP-based trend indicators and comparing current and historic MP-based trend indicators.

Optionally, the one or more processors may be configured to calculate the HF trend by calculating a CP-based trend indicator and an MP-based trend indicator. The classifying may comprise comparing the CP-based and MP-based trend indicators to corresponding thresholds to classify the patient condition as one of improved, deteriorated or no change. An implantable medical device (IMD) may be coupled to the multi-electrode LV lead. A local external device may be configured to wirelessly communicate with the IMD. The local external device may be configured to communicate over a network with a remote server. The one or more processors may comprise at least a first processor housed within the IMD and configured to perform at least the determining and identifying operations.

BRIEF DESCRIPTION OF THE DRAWINGS

FIG. 4D illustrates examples of site-to-site (STS) relative spacing for distal portions of an LV lead that may be shaped in accordance with embodiments herein.

FIG. 4E illustrates an example of an LV electrode combination and a waveform propagating from the distal and to the proximal end of the LV lead in accordance with embodiments herein.

DETAILED DESCRIPTION

Figure 1:
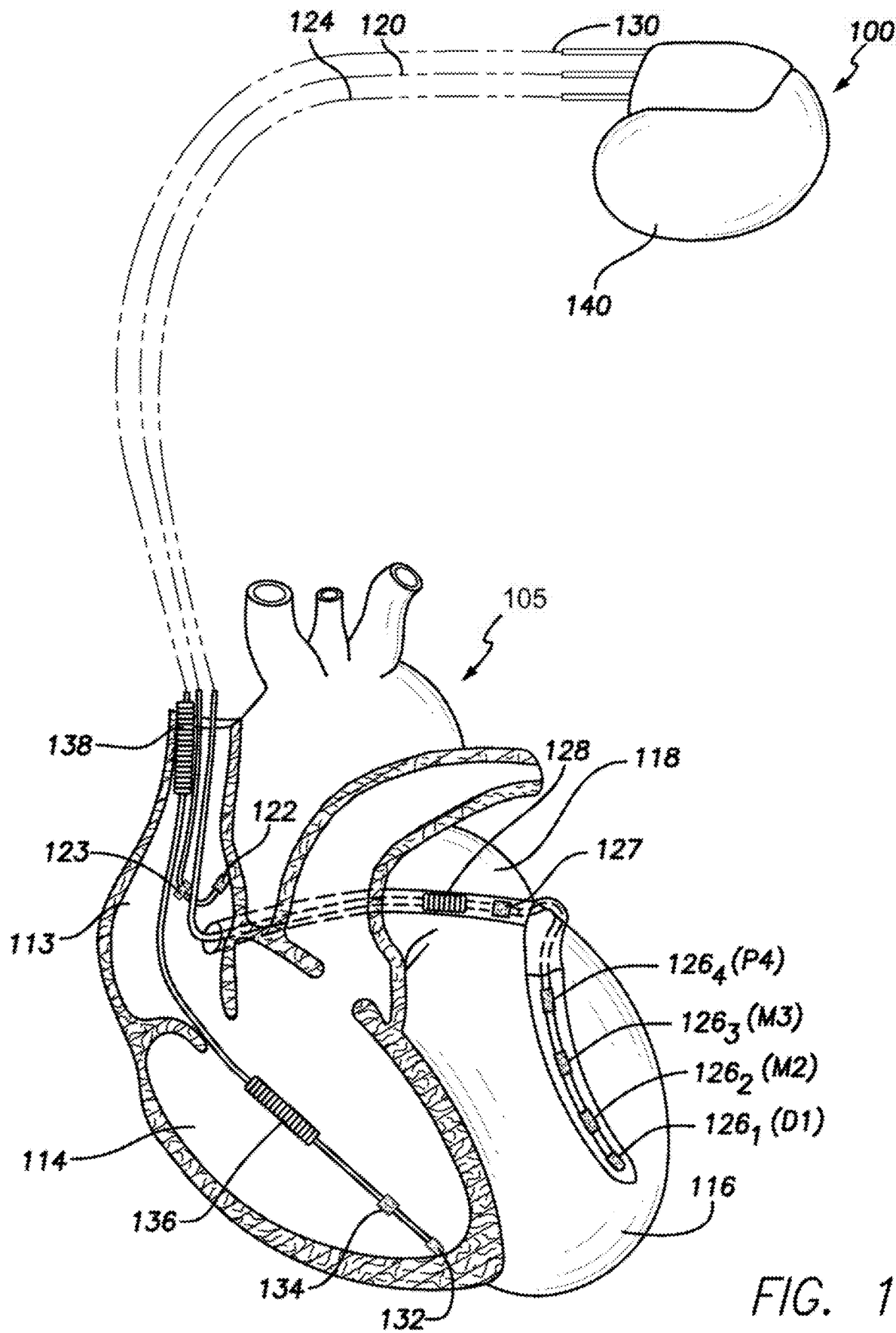
FIG. 1 illustrates an implantable medical device (IMD) in electrical communication with multiple leads implanted into a patient's heart for delivering multi-chamber stimulation and sensing cardiac activity according to an embodiment.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that other methods may be used in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

In accordance with embodiments herein, methods and systems are described to track long-term patient response to IMD therapies, such as CRT therapies. The long-term patient response tracks changes in (a) RV and LV electrode activation conduction patterns during intrinsic and/or paced conduction, and/or (b) EGM morphologies. For example, the long-term tracking may search for gradual changes that are expected in response to LV reverse remodeling. Embodiments herein identify differences in activation time across the 4 LV electrodes (D1, M2, M3, P4) during intrinsic RV-LV conduction over a select period of time. For example, the methods and systems herein may collect activation events daily, weekly, monthly and the like. The RV-LV activation times for the activation events sensed at the 4 LV electrodes can be averaged, wirelessly transmitted from an IMD to a local external device and uploaded over a wide area network to a remote medical network server, such as the Merlin.net™ network. The RV-LV activation times may be used to define conduction patterns indicative of a manner in which electrical wave fronts propagate through the left ventricular wall tissue. Over time, the conduction patterns change, thereby providing long-term trends that embodiments herein utilized to track various patient conditions, such as reverse remodeling. Additionally, embodiments herein collect and save daily averages of the EGM morphologies at the LV electrodes during paced/intrinsic RV-LV conduction. The EGM morphologies are tracked in a similar manner to provide trends over time.

Terms

The term "LV sensing site", as used herein, refers to the location of an LV electrode that at least partially defines a sensing vector or channel over which the delivered pacing pulse is sensed. For example, the multiple LV sensing sites correspond to the locations of the LV electrodes, such as D1, M2, M3, and P4 of a quadripolar LV lead. In an embodiment, the IMD senses along at least four sensing vectors, where each sensing vector utilizes a sensing cathode electrode in the left ventricle. The sensing vectors associated with the LV sensing sites may be unipolar vectors D1-CAN, M2-CAN, M3-CAN, and P4-CAN, where the CAN represents the anode electrode and D1, M2, M3 and P4 represent the cathode electrode. The pacing pulse is delivered at a RV pacing site and sensed at various LV sensing sites. This configuration may be referred to as RV pace—LV sense. Optionally, sensing vectors other than unipolar vectors may be used, such as D1-RV coil. In accordance with at least some embodiments, the sensing vectors are assigned to exclude LV electrodes as anodes and limit the LV electrodes to be cathodes.

The term "pacing site" refers to a location of a cathode that is used to deliver a pacing pulse along a pacing vector. For example, an RV pacing pulse may be delivered at the RV tip electrode or the RV ring electrode, along a pacing vectors RV tip to RV coil, or RV ring to RV coil, respectively. Optionally, the pacing vector may be unipolar between an RV cathode and the CAN. As another example, an RA pacing site may be at the atrial tip electrode or the atrial ring electrode, along the pacing vectors from the respective electrodes to the SVC coil or to the CAN.

FIG. 1 illustrates an implantable medical device (IMD) 100 in electrical communication with multiple leads implanted into a patient's heart 105 for delivering multi-chamber stimulation and sensing cardiac activity according to an embodiment. The IMD 100 may be a dual-chamber stimulation device, including an IMD, capable of treating both fast and slow arrhythmias with stimulation therapy, including cardioversion, defibrillation, and pacing stimulation, including CRT. Optionally, the IMD 100 may be configured for multi-site left ventricular (MSLV) pacing, which provides pacing pulses at more than one site within the LV chamber each pacing cycle. To provide atrial chamber pacing stimulation and sensing, IMD 100 is shown in electrical communication with a heart 105 by way of a left atrial (LA) lead 120 having an atrial tip electrode 122 and an atrial ring electrode 123 implanted in the atrial appendage 113. IMD 100 is also in electrical communication with the heart 105 by way of a right ventricular (RV) lead 130 having, in this embodiment, a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava. Accordingly, the RV lead 130 is capable of receiving cardiac signals and delivering stimulation in the form of pacing and shock therapy to the right ventricle 114 (also referred to as the RV chamber).

To sense left atrial and ventricular cardiac signals and to provide left ventricle 116 (e.g., left chamber) pacing therapy, IMD 100 is coupled to a multi-pole LV lead 124 designed for placement in the "CS region." As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes $126_1$, $126_2$, $126_3$, and $126_4$ (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes $126_1$, $126_2$, $126_3$, and $126_4$, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead. Although three leads 120, 124, and 130 are shown in FIG. 1, fewer or additional leads with various numbers of pacing, sensing, and/or shocking electrodes may optionally be used. For example, the LV lead 124 may have more or less than four LV electrodes 126.

The LV electrode $126_1$ is shown as being the most "distal" LV electrode with reference to how far the electrode is from the left atrium 118. The LV electrode $126_4$ is shown as being the most "proximal" LV electrode 126 to the left atrium 118. The LV electrodes $126_2$ and $126_3$ are shown as being "middle" LV electrodes, between the distal and proximal LV electrodes $126_1$ and $126_4$, respectively. Accordingly, so as to more aptly describe their relative locations, the LV electrodes $126_1$, $126_2$, $126_3$, and $126_4$ may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The LV electrodes 126 are configured such that each electrode may be utilized to deliver pacing pulses and/or sense pacing pulses (e.g., monitor the response of the LV tissue to a pacing pulse). In a pacing vector or a sensing vector, each LV electrode 126 may be controlled to function as a cathode (negative electrode). Pacing pulses may be directionally provided between electrodes to define a pacing vector. As explained herein, combinations of LV electrodes 126 are paired with one another to operate as a common virtual electrode, such as a common virtual cathode, when delivering pacing therapies. In a pacing vector, a generated pulse is applied to the surrounding myocardial tissue through the cathode. The electrodes that define the pacing vectors may be electrodes in the heart 105 or located externally to the heart 105 (e.g., on a housing/case device 140). For example, the housing/case device 140 may be referred to as the CAN 140 and function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g., vectors between an LV electrode 126 and the RV coil 136 or another electrode remote from the left ventricle 116). Below is a list of exemplary bipolar sensing vectors with LV cathodes that may be used for sensing using the LV electrodes D1, M2, M3, and P4 and the RV coil 136. In the following list, the electrode to the left of the arrow is assumed to be the cathode, and the electrode to the right of the arrow is assumed to be the anode.

D1→RV coil
M2→RV coil
M3→RV coil
P4→RV coil
D1→M2
D1→P4
M2→P4
M3→M2
M3→P4
P4→M2

It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode. Below is a list of exemplary bipolar pacing vectors with LV cathodes that may be used for pacing using the LV electrodes D1, M2, M3, and P4 and the RV coil 136. In the following list, the electrodes to the left of the arrow are assumed to be cathodes, and the electrode to the right of the arrow is assumed to be the anode.

D1→RV coil (or CAN)+M2→RV coil (or CAN)
M2→RV coil (or CAN)+M3→RV coil (or CAN)
M3→RV coil (or CAN)+M4→RV coil (or CAN)
M2→RV coil (or CAN)+M3→RV coil (or CAN)+P4→RV coil (or CAN)
D1→RV coil (or CAN)+M2→RV coil (or CAN)+M3→RV coil (or CAN)

It is noted that the preceding list is only a subset of the available pacing and sensing vectors for use with the IMD 100. Further, when delivering a series of pacing pulses, one of the above pacing vectors is used for at least the first pacing pulse in the series. Other pacing vectors may be used for subsequent pulses in the series of pacing pulses. Furthermore, additional pacing pulses may be generated in other chambers of the heart, such as the right ventricle.

Conduction Pattern

Activation times can provide an accurate surrogate for heart failure status. For example, one trend indicator may relate to RV-LV conduction delay.

Figure 4A:
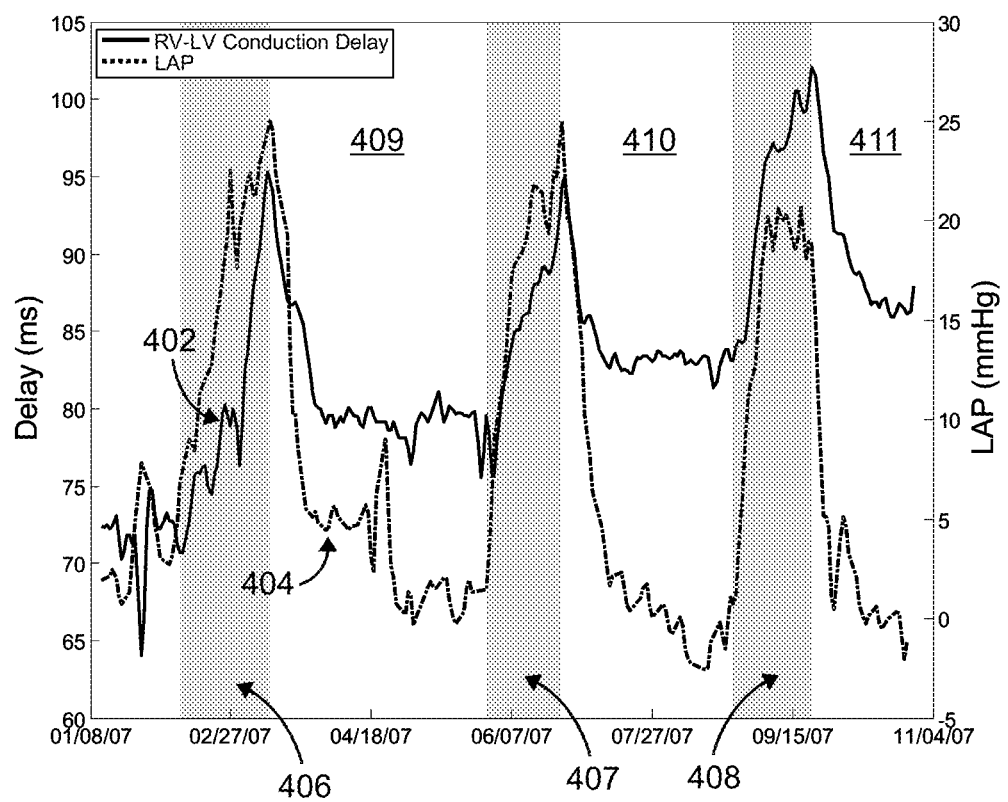
FIG. 4A illustrates an example of a relation between RV-LV conduction delay, left atrial pressure (LAP) during rapid pacing induced heart failure in accordance with embodiments herein.

FIG. 4A illustrates an example of a relation between RV-LV conduction delay, left atrial pressure (LAP) during rapid pacing induced heart failure. FIG. 4A plots a time period between January and November 2007 along the horizontal axis, RV-LV delay in milliseconds along the left vertical axis and left atrial pressure in millimeters of mercury along the right vertical axis. The RV-LV delay 402 is shown in a solid line, while the LAP 404 is shown in a dashed line. The grade regions indicate rapid pacing time periods 406-408 during which a patient experienced induction of heart failure. The induced heart failure occurred during time periods in which the patient's implantable medical device was program to provide rapid pacing. The rapid pacing functionality was turned off during the intervals 409-411. During the intervals 409-411, the patient experienced recovery or reverse heart modeling away from an HF condition.

As shown in FIG. 4A, the RV-LV delay 402 and the LAP 404 experienced spikes during the rapid pacing time periods 406-408. The RV-LV delay 402 and the LAP 404 dropped to substantially lower levels during the intervals 409-411 during which rapid pacing was turned off. From the trends exhibited in FIG. 4A, it can be seen that RV-LV conduction delay increases over time during the induction of HF. Thus, the conduction delay between the RV and LV provides a good surrogate for HF status. The correlation between HF progression and RV-LV conduction time can be extrapolated to the conduction times and conduction pattern across the RV electrode and all 4 LV electrodes, for a quadripolar LV lead (e.g., Quartet®). Similarly, the changes in conduction non-uniformity in response to remodeling (or reverse remodeling) can be tracked and viewed as long-term trends to follow HF progression over time. In accordance with embodiments herein, changes in the electrical conduction patterns are identified and utilized to classify heart failure remodeling.

HF Progression Monitoring

Conduction patterns and EGM morphologies generally uniquely correspond to different stimulus origins, myocardial structures, and the underlying electrophysiology. During intrinsic RV-LV conduction, the stimulus origin may generally remain the same over time, whereas the myocardial structure and underlying electrophysiology will change as ventricular remodeling progresses or reverses. The changes in myocardial structure and underlying electrophysiology generally represent electromechanical changes. Long-term electromechanical changes can be captured over weeks and months by collecting conductions patterns and tracking gradual alterations in the RV-LV activation pattern across the 4 LV electrodes. The following discussion describes (A) example activation pattern metrics associated with conduction patterns over HF progression, (B) morphology metrics associated with different EGM morphologies over HF progression, and (C) the overall assessment of HF by identifying trends in the conduction patterns and morphologies.

Figure 2:
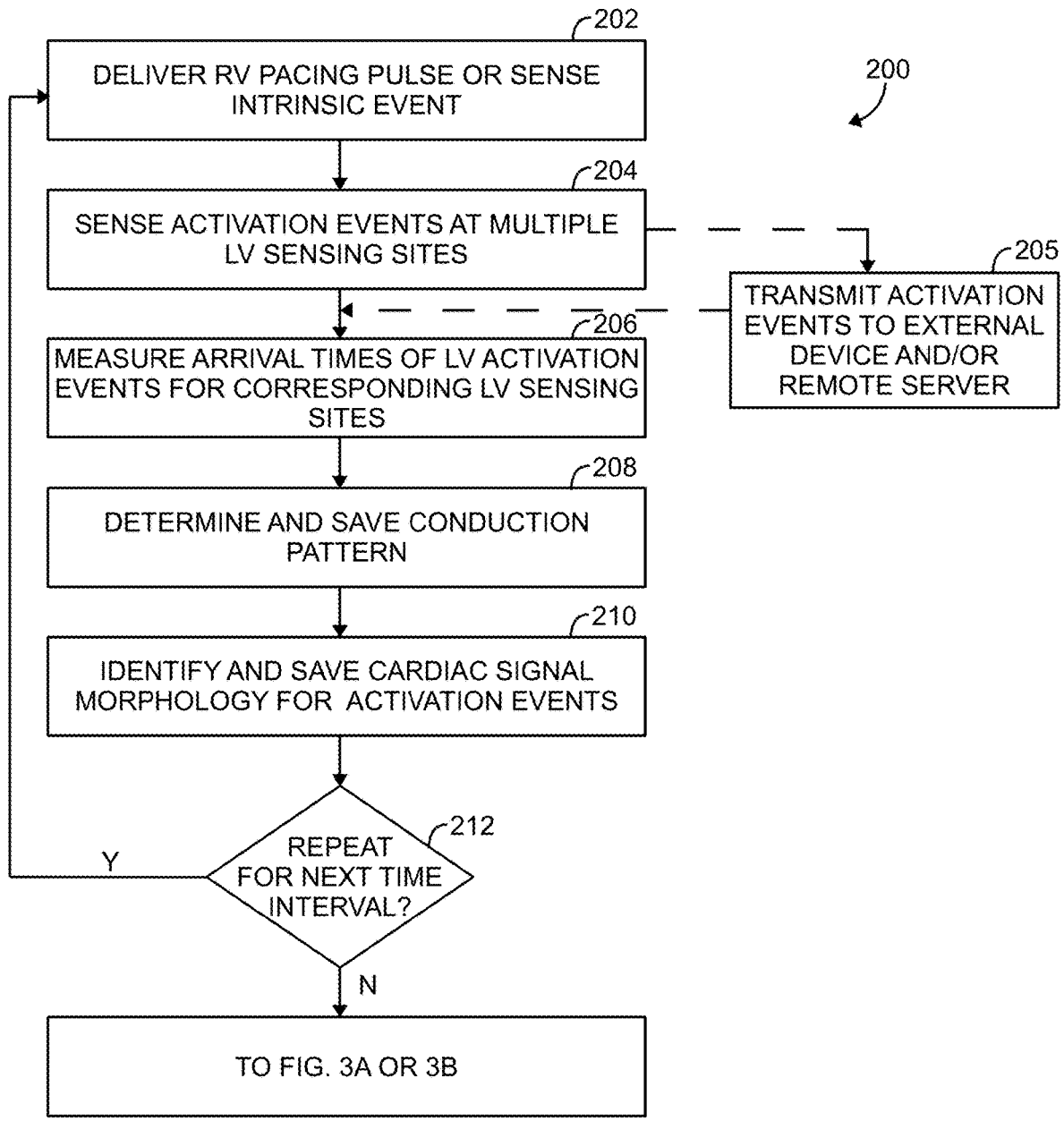
FIG. 2 illustrates the one or more processors utilizing the arrival times to determine a conduct pattern (CP) across the LV sensing sites in accordance with embodiments herein.
Figure 3A:
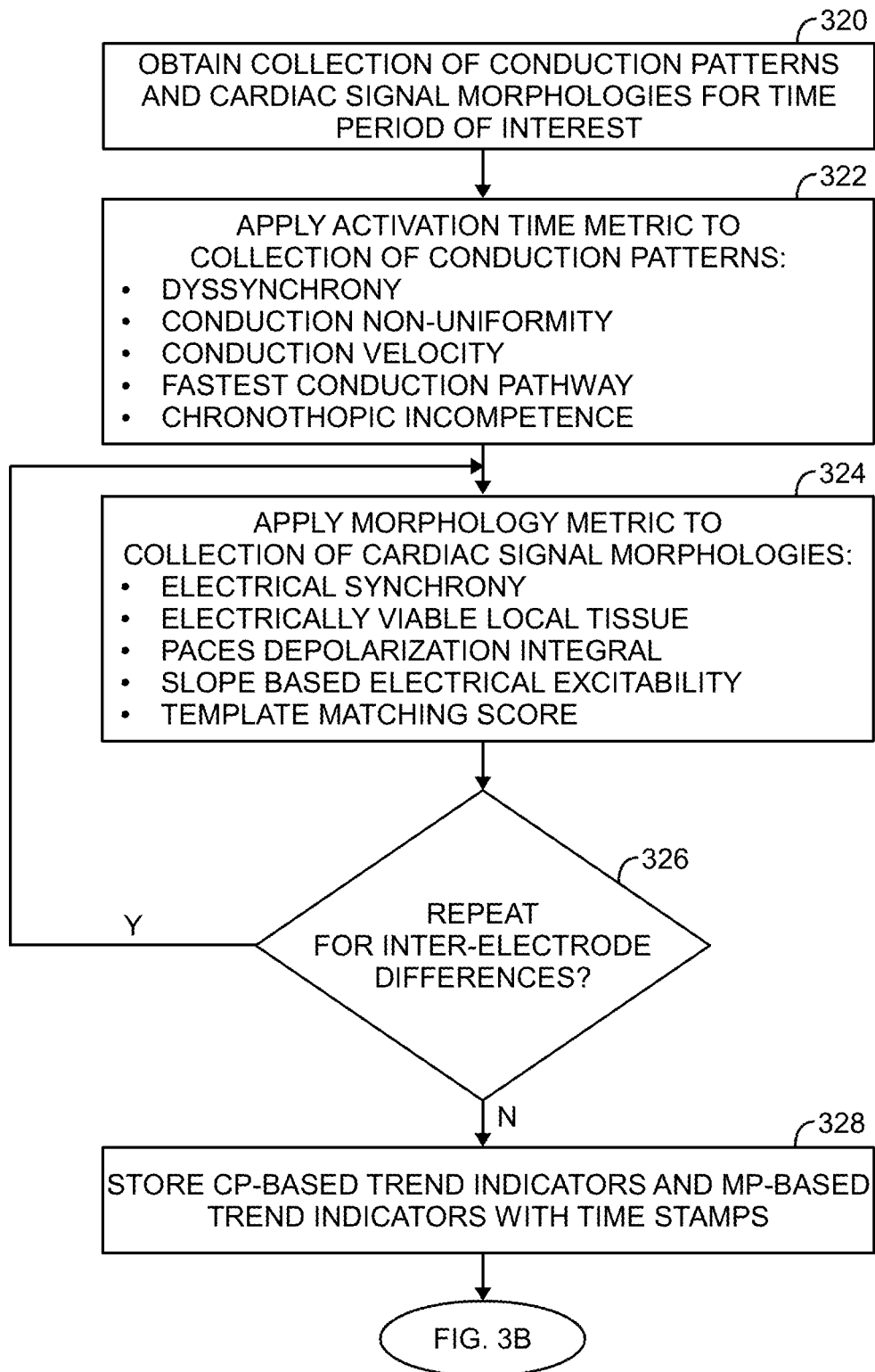
FIG. 3A illustrates a process for calculating an HF trend based on the CP collection and morphology (MP) collection recorded in connection with the operations of FIG. 2 in accordance with an embodiment herein.
Figure 3B:
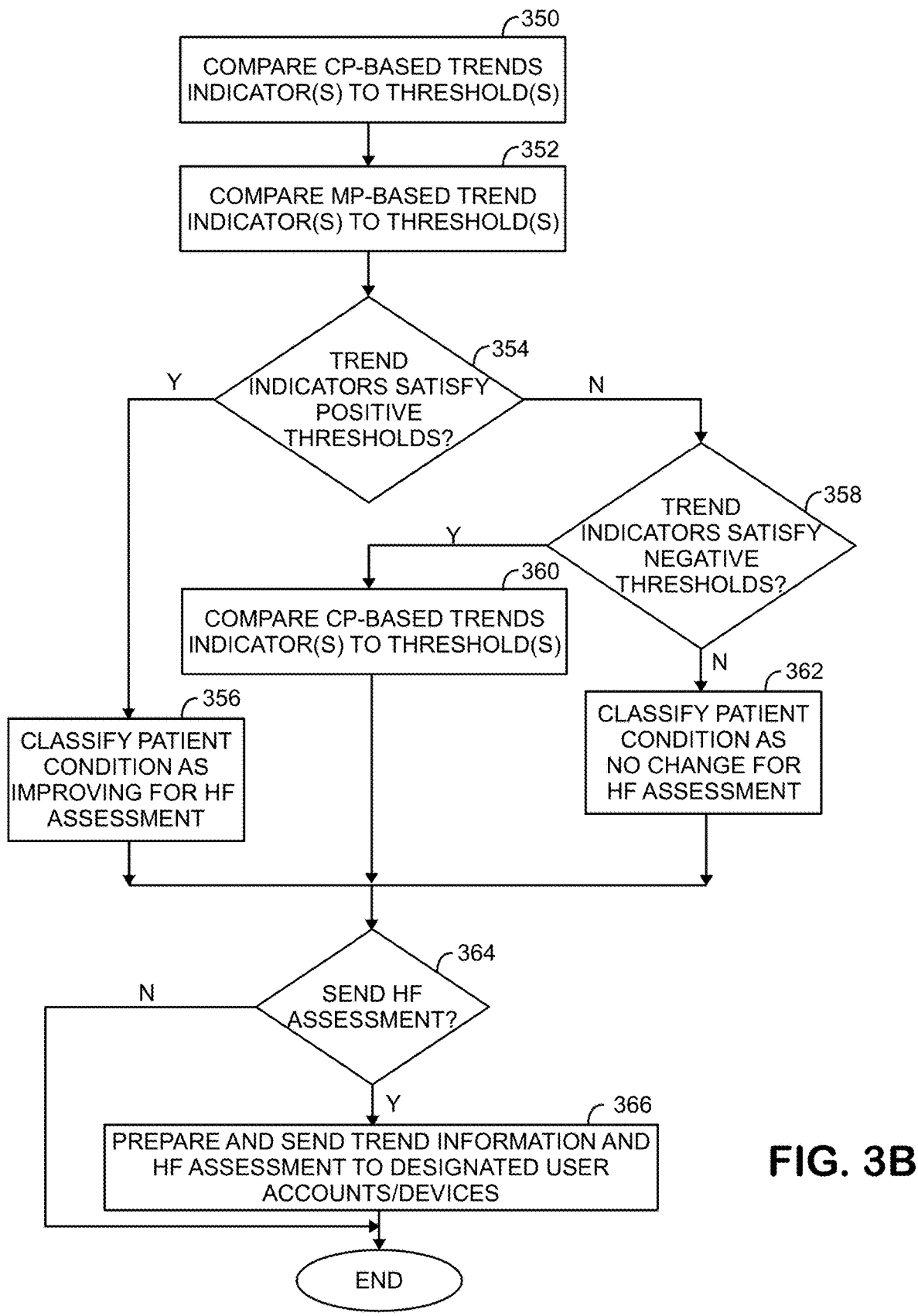
FIG. 3B illustrates a process for classifying a patient condition based on trend indicators to form an HF assessment and to provide notifications of the HF assessment in accordance with embodiments herein.

FIGS. 2 and 3A-3B illustrate a process for monitoring trends and heart failure progression in accordance with embodiments herein. The process 200 may be performed in whole or in part by the IMD 100. Optionally, a local external device and/or remote server may perform all or portions of the processes described herein utilizing activation events sensed by the IMD 100. In various embodiments, certain aspects of the process 200 may be omitted or added, certain aspects may be combined, certain aspects may be performed simultaneously, certain aspects may be performed concurrently, certain aspects may be split into multiple aspects, certain aspects may be performed in a different order, or certain aspects or series of aspects may be re-performed in an iterative fashion. In general, it is contemplated that the process of FIGS. 2 and 3A-3B will be performed in an unsupervised out of clinic environment, however, the process may be performed in whole or in part in a clinic under the supervision of a clinician.

At 202, an intrinsic ventricular event occurs or a paced ventricular event (e.g., pacing pulse) is delivered from at least one RV or RA pacing site. For a paced event, the pacing pulse is generated by the pulse generator 170 and/or the pulse generator 172, depending on the therapy pacing site selected. The pacing pulse may be delivered by the microcontroller 160 by sending a control signal to one or both pulse generators 170, 172 that identifies the pacing vector, the electrical output, the timing, and the like. The pulse generator 170 and/or 172 in response generates an electrical potential at one or both electrodes that define a selected pacing vector, resulting in a potential difference between the electrodes that induces a depolarization wave in the surrounding heart tissue. The depolarization wave propagates along a wave front that varies in shape, timing and velocity based on, among other things, a health of the heart wall.

At 204, LV activation events are sensed at corresponding LV sensing sites. For example, when four LV electrodes are utilized as separate sensing sites, four LV activation events are sensed. In the present example, a set of four LV activation events are generated in response to a single paced or intrinsic event. The LV activation events are detected at individual LV sensing sites as the propagating depolarization wave front crosses the corresponding LV electrodes.

In an embodiment, the LV activation events are sensed by at least one sensor. For example, the sensor may be the ventricular sensing circuit 184, which includes an amplifier. For example, sensed electrical activity (e.g., voltage and/or current) at each electrode in a sensing vector may be routed as signals through the electrode configuration switch 174 to the ventricular sensing circuit 184. The ventricular sensing circuit 184 may amplify, convert, and/or digitize the received signals before forwarding the signals to the microcontroller 160 for recordation and analysis of the data. Optionally, various other sensors and/or sensing circuits may be used to sense the LV activation events instead of or in addition to the ventricular sensing circuit 184.

An optional operation is illustrated at 205. At 205, a transceiver of an IMD may transmit the activation events as sensed to an external device which may then convey the activation events to a remote server. The information transmitted at 205 may include digitize representations of a raw analog sensed signals as sensed at each LV sensing site. For example, a transmission may include a set of digitized sensed signals for a predetermined period of time (e.g., a number of milliseconds), where each digitized sensed signal corresponds to a different LV sensing electrode. Optionally, the operation at 205 may be omitted entirely.

At 206, one or more processors measure arrival times of the LV activation events for corresponding LV sensing sites (e.g., by the conduction pattern detector 163 and/or CPU 602). The arrival times (e.g., conduction delays) may correspond to a conduction time from delivery of the pacing pulse until sensing of the corresponding LV activation event. For example, arrival times may be measured by recording the time (e.g., designated as time To) that a pacing pulse is delivered at an RV site, recording the times (e.g., designated as times $T_{D1}$, $T_{M2}$, $T_{M3}$, $T_{P4}$) of the LV activation events at each of the LV sensing sites, and subtracting the time of the pacing pulse from the times of the LV activation events (e.g., $T_0$-$T_{D1}$). Optionally, the arrival times may be measured using an internal timer (associated with each sensing site for each sensing circuit) by starting the timer when the pacing pulse is delivered and stopping the timer when each LV activation event occurs to determine the arrival time of each respective LV activation event. Optionally, in connection with an intrinsic event, the arrival times may be measured using an internal timer by starting the timer when the intrinsic event is sensed at an RV sensing site and stopping the timer when each LV activation event occurs to determine the arrival time of each respective LV activation event. As an example, if it takes 60 ms after an RV pacing pulse (or intrinsic RV event) for the sensor (e.g., sensing circuit 184) to detect an LV activation event at an LV sensing site, then the arrival time for that LV sensing site is 60 ms. The arrival times at the different LV sensing sites may vary due to the difference in locations of the LV electrodes relative to the cathode at the RV pacing site. Due to the different relative locations, the propagation wave may reach some LV sensing sites sooner than other sensing sites, resulting in a shorter arrival time.

Optionally, the arrival times may be measured by the external device 600 and/or a remote server. In order to afford external measurement, the IMD 100 may convey raw sensed data to a local remote device and/or remote server. For example, the local remote device may be a smart phone, tablet device, laptop computer, Merlin™ programmer (developed by St. Jude Medical, Inc.) and the like. The external device and/or remote server analyze the raw sensed data and determine the time from the RV pacing or intrinsic marker to LV activation at each of the LV sensing sites (e.g., D1-CAN, M2-CAN, M3-CAN, P4-CAN).

Figure 4B:
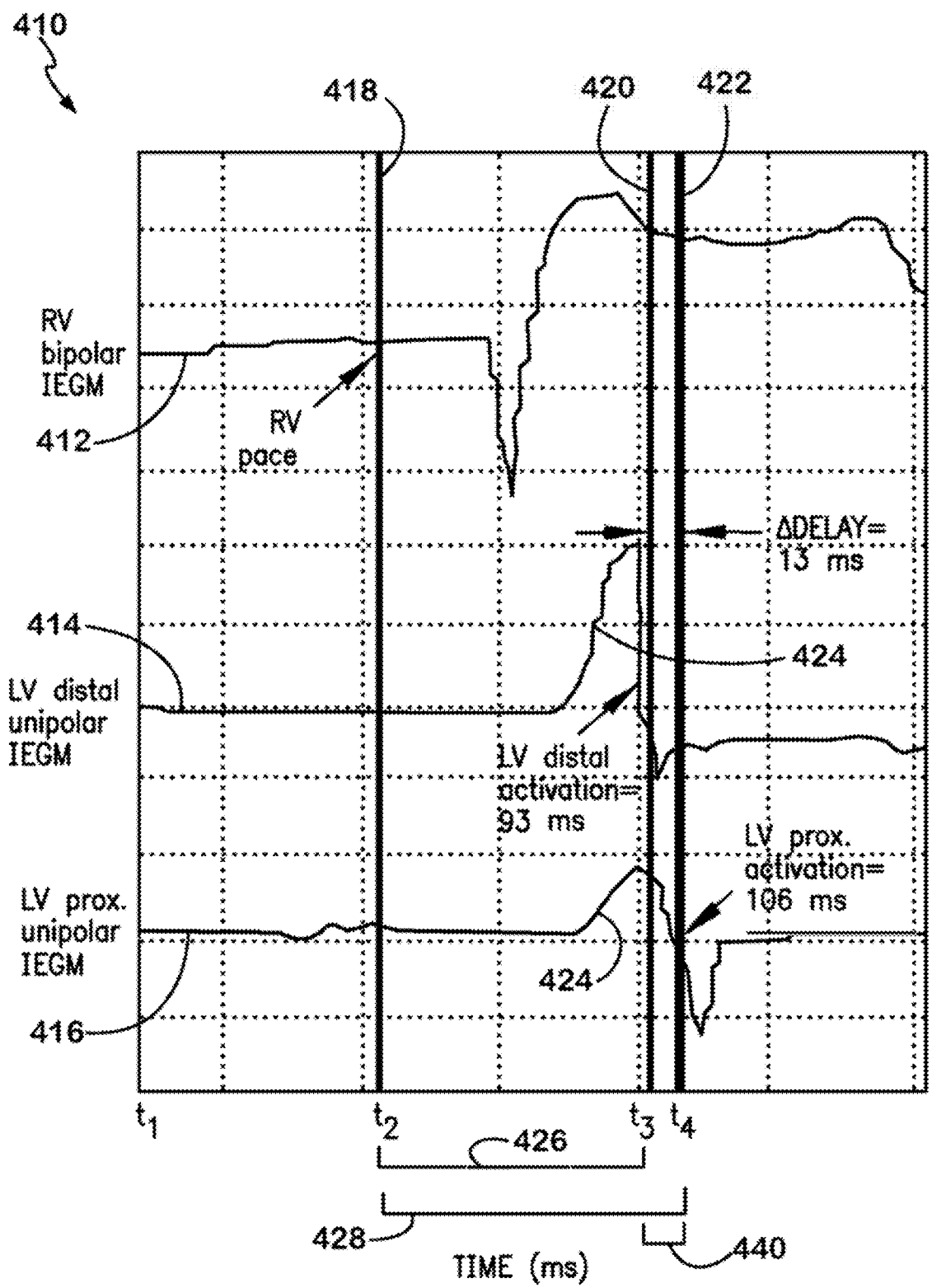
FIG. 4B illustrates a graph plotting multiple data streams (e.g., cardiac signals) measured in connection with different sensing sites in accordance with embodiments herein.

FIG. 4B illustrates a graph 410 plotting multiple data streams (e.g., cardiac signals) measured in connection with different sensing sites. The data streams are displayed as intracardiac electrogram (IEGM) waveforms representative of the electrical activity in ventricular tissue (measured in mV) over time (measured in ms). The graph 410 displays an IEGM waveform 412 associated with an RV electrode and two IEGM waveforms 414, 416 associated with an LV distal electrode and an adjacent LV electrode, respectively. The three IEGM waveforms 412-416 may be representative of the electrical activity sensed along sensing vectors at least partially defined by the respective corresponding electrodes. The graph 410 displays the waveforms 412-416 vertically separated in order to compare the shape of the waveforms 412-416 over time. It should be recognized that the waveforms 412-416 share a common time scale but may not share the same electrical activity scale, meaning that the vertical distance between one waveform from the other waveforms does not represent a difference in the measured mV.

The graph 410 illustrates how arrival times of LV activation events may be measured at operation 206 of process 200 (shown in FIG. 2) as well as how site-to-site (STS) relative delays may be calculated. For example, each of the sensing vectors may begin sensing for electrical activity at time $t_1$. At time $t_2$, an RV pacing pulse is delivered at an RV pacing site, which is denoted on the graph 410 by an RV pace marker 418. As the depolarization wave propagates through the myocardial tissue, the activity sensed at the RV and LV sensing sites are recorded in the waveforms 412-416. For example, the wave is used for biventricular (BiV) pacing, as the pulse delivered in the right ventricle propagates to the left ventricle where it is sensed at the LV sensing sites. The LV distal electrode waveform 414 indicates the presence of an LV activation event at time $t_3$, while the LV adjacent electrode waveform 416 indicates an LV activation event afterwards at time $t_4$. The LV activation events for the LV distal electrode and the LV adjacent electrode are denoted by activation event markers 420 and 422, respectively.

As shown in graph 410, the activation event markers 420, 422 represent the midpoint of the negative slope of the R-wave 424, which represents intrinsic ventricular depolarization, or the maximum negative slope of the R-wave 424. Optionally, the markers 420, 422 may be located at other locations along the R-waves 424 of the waveforms 414, 416, as long as the location selected is the same for both waveforms 414, 416, for comparison purposes. For example, the markers 420, 422 optionally may be located at the starting point of the R-wave 424 (e.g., leftmost location with a positive amplitude), the midpoint of the positive slope of the R-wave 424, the point of maximum positive slope, the apex of the R-wave 424, the nadir or lowest point of the R-wave 424, and the like. The markers 420, 422 are positioned automatically, and the arrival times and STS relative delays calculated automatically, by the IMD 100, local external device and/or remote server without assistance from a clinician or another third party.

Once the LV activation events 420, 422 are determined, the arrival times for each of the LV sensing sites are computed by measuring the time between the time of the RV pacing marker 418 and the times of the activation events 420, 422. For example, the LV activation event 420 for the LV distal electrode occurs at time $t_3$, the RV pacing marker 418 occurs at time $t_2$, so the arrival time 426 for the LV sensing site at the LV distal electrode is the difference between times $t_3$ and $t_2$. As shown in FIG. 4B, that difference was measured to be 93 ms, which represents the arrival time 426 of the LV activation event 420 at the LV distal sensing site. Likewise, the arrival time 428 for the LV activation event 422 at the LV proximal sensing site is represented as the time difference between the event 422 at time $t_4$ and the pacing pulse at time $t_2$, which is measured to be 106 ms. Since the arrival times 426, 428 for respective LV distal and proximal sensing sites are known, the STS relative delay between these two sensing sites may be calculated as the difference between the two times 426, 428. For example, as shown in FIG. 4, the STS relative delay (e.g., Δdelay) 440 for the combination of the LV distal sensing site and the LV proximal sensing site is 13 ms, calculated by subtracting 93 ms from 106 ms. The 13 ms delay 440 represents the time delay from time $t_3$ to time $t_4$.

Returning to FIG. 2, at 208, the one or more processors utilizes the arrival times to determine a conduct pattern (CP) across the LV sensing sites. The conduction pattern is saved along with a timestamp indicating a time at which the conduction pattern was sensed. Additionally or alternatively, other information may be recorded with the conduction pattern. For example, the microcontroller 160 and/or CPU 602 may calculate a difference between the arrival times for a select combination of the adjacent electrodes to obtain a site-to-site (STS) relative delay between the select combination of the adjacent LV sensing sites. For example, STS relative delay$_{D1,M2}$ for the electrode combination D1+M2 may be calculated by subtracting the arrival time associated with the LV sensing site at the D1 electrode from the arrival time associated with the LV sensing site at the M2 electrode. Therefore, if the arrival time at sensing site D1 is measured to be 80 ms, and the arrival time at sensing site M2 is 87 ms, the STS relative delay$_{D1, M2}$ would be the difference, 7 ms. The STS relative delays may be calculated by the delay calculation (DC) module 168 within the microcontroller 160, and/or the CPU 602.

Figure 4C:
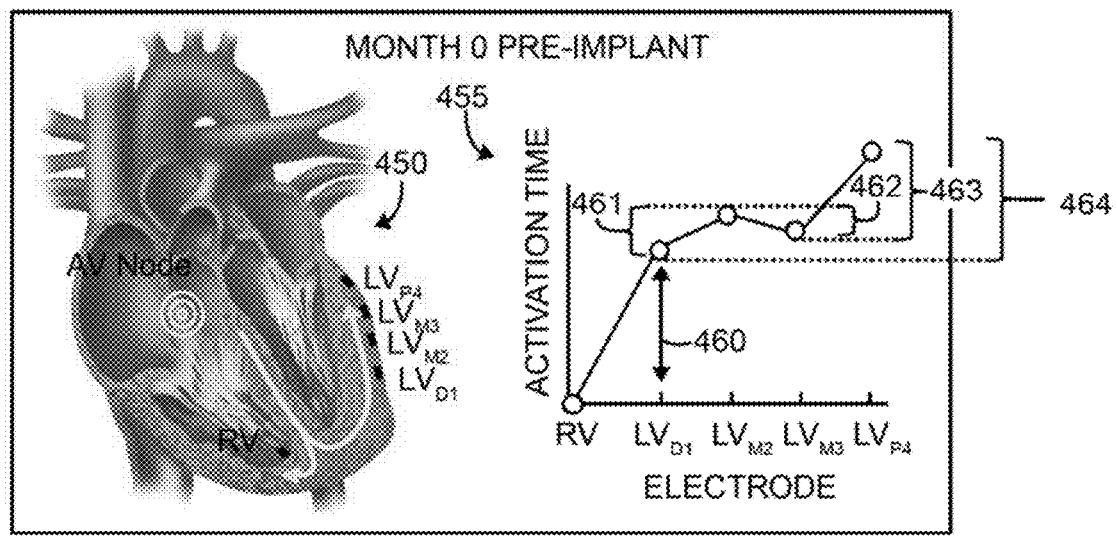
FIG. 4C illustrates examples of conduction patterns that may be determined at different points in time for an individual patient in accordance with embodiments herein.
Figure 4C:
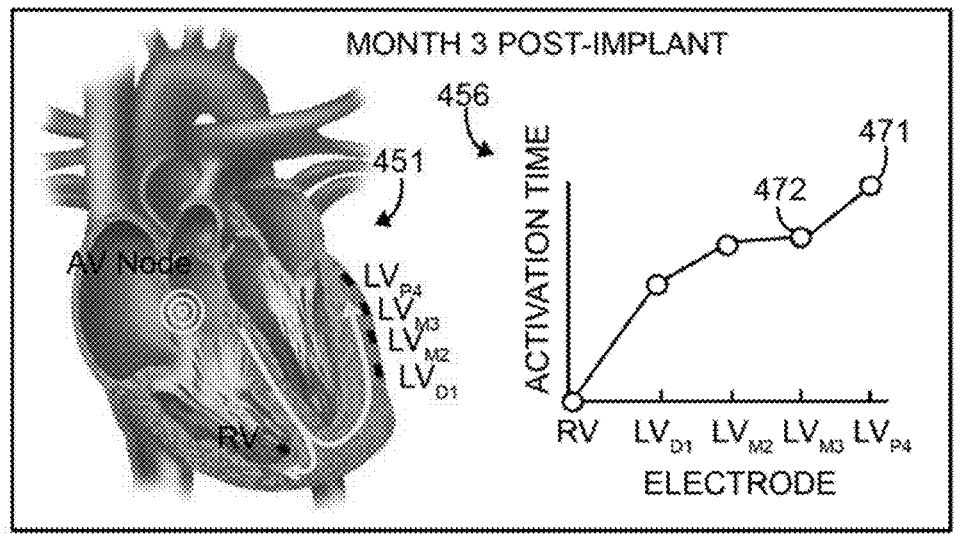
Figure 4C:
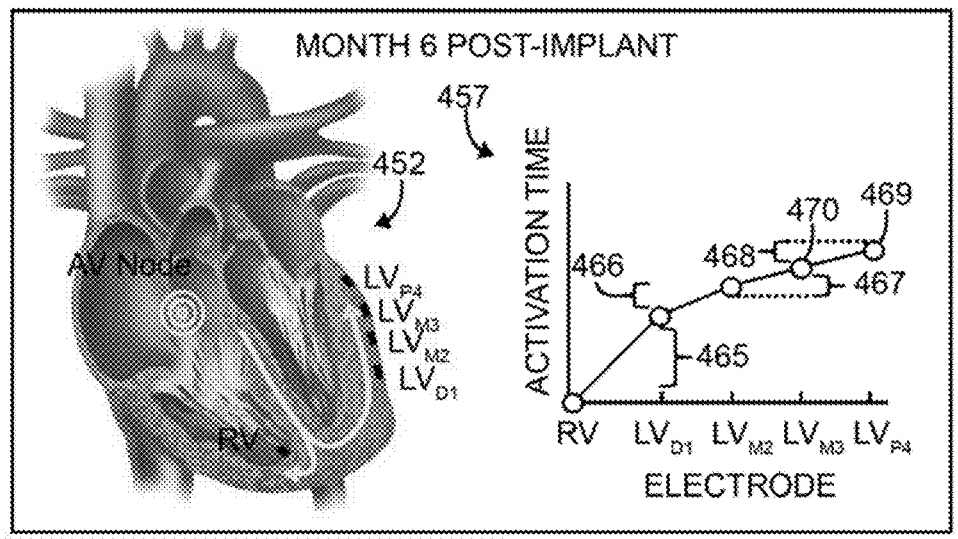

FIG. 4C illustrates examples of conduction patterns that may be determined at different points in time for an individual patient. Panels A-C illustrate examples of conduction patterns during intrinsic conduction demonstrating reverse remodeling. Panel A corresponds to a select point in time before an IMD is implanted, while panels B and C correspond to select points in time at 3 months post implant and 6 months post implant. The panels A-C graphically illustrate schematics or propagation wave fronts 450-452 to show the pathway of propagation across the RV and 4 LV electrodes. The propagation wave fronts 450-452 differ from one another as the health of the heart wall has changed (exhibits reverse modeling) between the pre-implant, 3 month and 6 month points in time. Panels A-C also illustrate conduction patterns 455-457 that are determined at 208. The conduction patterns 455-457 illustrate the order of activation times for the RV and four LV electrodes. The gradual change in activation pattern of the RV and LV electrodes can highlight a reduction in electrical dyssynchrony that follows ventricular reverse remodeling. The conduction patterns 455-457 illustrate the LV sensing site (LV electrode) along the horizontal axis and the activation time along the vertical axis. At pre-implant, the patient exhibited a large difference in arrival time 460 between the intrinsic or paced event at the RV site and the distal $LV_{D1}$ sensing site followed by a shorter difference in arrival time 461 between the distal $LV_{D1}$ and second middle $LV_{M2}$ sensing sites. The third middle $LV_{M3}$ sensing site sensed the conduction pattern 455 (propagation wave front) an arrival time 462 before the second middle LV sensing site $LV_{M1}$, while the fourth proximal $LV_{P4}$ sensing site sensed the propagation wave front a relatively longer arrival time 462 after the third middle $LV_{M3}$.

The conduction pattern 456, exhibited 3 months after implant, differs from the conduction pattern 455 pre-implant. The conduction pattern 456 has an arrival time at the third middle $LV_{M3}$ sensing site that does not follow the arrival time at the second middle $LV_{M2}$ sensing site, thereby indicating an improvement in the electromechanical properties of the local heart tissue in the region between the second and third middle $LV_{M2}$ and $LV_{M3}$ sensing sites. The conduction pattern 457 exhibited 6 months after implant shows a healthier myocardial condition as compared to the conduction pattern 456 exhibited 3 months after implant. In particular, the activation times of the conduction pattern 457 have generally even differences in activation time 465-468 there between. Six months after implant, the activation time 469 for $LV_{P4}$ sensing site occurred evenly after the activation time 470 for $LV_{M3}$ sensing site, which shows an improvement over the activation times 471, 472 for $LV_{P4}$ and $LV_{M3}$ sensing sites.

FIG. 4D illustrates examples of STS relative spacing for distal portions of an LV lead that may be shaped in accordance with embodiments herein. Within FIG. 4D, the distal portions 702, 704 and 706 may correspond to a common lead, but bent in different manners based upon the venous branch. The distal portions 702, 704 and 706 each include LV electrodes P4, M3, M2 and D1. The electrodes P4 and M3 have an STS axial spacing 716. The electrodes M3 and M2 have an STS axial spacing 718. The electrodes M2 and D1 have an STS axial spacing 720. The distal portion of the LV lead may be shaped in different manners based upon the venous branch in which the lead is placed. For example, the distal portion 706 may be positioned in a venous branch which maintains the distal portion in a relatively straight manner. Alternatively, the distal portion 704 may be positioned in a venous branch that slightly bends the distal portion. Alternatively, the distal portion 702 may position in a venous branch that substantially bends the lead, such as in an S-shape.

When the LV lead is shaped corresponding to the distal portion 706, the STS axial spacing 716-720 between the electrodes (P4, M3, M2 and D1) along the longitudinal axis of the lead generally may be used as the STS relative spacing. However, when the LV lead is shaped, corresponding to the distal portion 702, the axial spacing between the electrodes (P4, M3, M2 and D1) does not necessarily correspond to the actual STS relative spacing. Instead, the electrodes M2 and D1 may have an STS relative spacing 710 that is less than the axial spacing 720. Similarly, the electrodes P4 and M3 may have an STS relative spacing 714 that is less than the axial spacing 716.

Returning to FIG. 2, at 208, the microcontroller 160 and/or CPU 602 calculate conduction patterns based on the arrival times and/or difference in arrival times at the LV sensing sites. For example, attention is directed to FIG. 4E. FIG. 4E illustrates an example of an LV electrode combination and a waveform propagating from the distal and to the proximal end of the LV lead. In FIG. 4E, arrows 750 represent a direction of electrical wave front propagation, where the wave front arrives at electrode D1 at time $T_1$, electrode M2 at time $T_2$, electrode M3 at time $T_3$ and electrode P4 at time $T_4$.

At 210, the one or more processors may identify morphologies (MPs) for cardiac signals associated with the LV activation events. The processors analyze the cardiac signals in connection with each LV electrode for the corresponding LV activation events. As one simple example, the identification of the morphologies may simply include recording the cardiac signals as a digitized signal in connection with each LV electrode. Additionally or alternatively, the cardiac signals may be analyzed in more detail, such as to identify peaks and valleys within the signal, total energy, and other characteristics of the cardiac signals that define morphology. The morphology is saved along with a timestamp indicating a time at which the cardiac signals having the morphology were sensed. Additionally or alternatively, other information may be recorded with the morphology.

At 212, the one or more processors may wait a predetermined period of time corresponding to a select time interval and then return flow to 202 to repeat the operations at 202-210. The operations at 202-210 are repeated at select intervals, such as hourly, daily, weekly and the like, to build a CP collection and an MP collection. The CP collection includes a set of conduction patterns recorded over the select interval, while the MP collection includes a set of morphologies recorded over the select interval. Next, flow may move to the operations at FIG. 3A or 3B.

FIG. 3A illustrates a process for calculating an HF trend based on the CP collection and MP collection recorded in connection with the operations of FIG. 2 in accordance with an embodiment herein. The operations of FIG. 3A may be performed by one or more processors of an implantable medical device, a local external device and/or a remote server.

At 320, the one or more processors obtain the CP collection and the MP collection for a time period of interest. By way of example only, the obtaining operation at 320 may include at least one of i) accessing memory of an external device or remote server where the CP collection and MP collection are stored, ii) receiving the CP collection and MP collection over a wireless communications link between the IMD and a local external device, and/or iii) receiving the CP collection and MP collection at a remote server over a network connection. The obtaining operation, when from the perspective of an IMD, may include sensing new conduction patterns and new morphologies in real time, and/or accessing memory to read a stored CP collection and stored MP collection from memory within the IMD. The obtaining operation, when from the perspective of a local external device, includes receiving the CP collection and MP collection at a transceiver of the local external device where the CP and MP collections are transmitted from an IMD and/or a remote server. The obtaining operation may be from the perspective of a remote server, such as when receiving the CP collection and MP collection at a network interface from a local external device and/or directly from an IMD. The remote server may also obtain the CP and MP collection from local memory and/or from other memory, such as within a cloud storage environment and/or from the memory of a workstation or clinician external programmer.

As displayed hereafter, the operations at 322 calculate a CP-based trend indicator by applying an AT metric to the CP collection, while the operations at 328 calculate an MP-based trend indicator by applying an MP metric to the MP collection. As explained further below, the process of FIG. 3B calculates HF trend based on the CP-based and MP-based HF indicators.

At 322, the one or more processors apply one or more activation time (AT) metrics or templates to the conduction pattern collection to calculate one or more CP trend indicators. The processors may implement specific activation time metrics that can be used to assess the HF disease status of a patient (i.e., improving vs. deteriorating) and presented to the clinician. The server, local device and/or IMD can be programmed to send a notification message to the clinician if any of these metrics change (positive or negative) beyond a preset threshold, signaling the clinician if an in-clinic assessment is recommended. The AT metric may comprise at least one of a dyssynchrony metric, conduction nonuniformity metric, conduction velocity metric, fastest conduction pathway metric or chronotropic incompetence metric. Activation time metrics may include, but are not limited to, the following metrics discussed hereafter.

As one example, the activation time metric may correspond to a difference in activation times between combinations of the RV and LV sensing sites/electrodes. For example, the processors may determine the difference in activation times between one or more combinations of RV and LV sensing sites (e.g., RV-LV D1, RV-LV M2, RV-LV M3, RV-LV P4), as well as between one or more combinations of LV sensing sites (e.g., LV D1-LV M2, LV M2-LV M3, LV M3-LV P4). The processors determine a select activation time difference (also "select AT difference") between a pair of sensing sites that satisfies a criteria of interest, such as a maximum difference in activation times. General dyssynchrony can be quantified by the maximum difference in activation times among the RV and LV electrodes, namely the pair of sensing sites for which a corresponding activation time difference is the greatest. For example, the select (e.g., maximum) activation time difference may correspond to the LVP4 and RV sensing sites. The processors analyze the conduction pattern, associated with an individual intrinsic or paced event to identify the activation time differences between combinations of sensing sites and to identify the maximum difference activation time associated with the individual intrinsic or paced event. At 322, the processors analyze the maximum difference activation times in connection with each conduction pattern in the CP collection. For example, a set of 20 conduction patterns in a CP collection would similarly have 20 corresponding select AT differences indicative of a heart condition at the time the corresponding conduction patterns were collected. As explained in connection with FIG. 3B, at 350-362, the processors determine whether the CP-based trend indicator, namely select AT differences between the conduction patterns, increases over time, decreases over time or remains substantially constant. When the CP-based trend indicator (e.g., select AT difference) reduces over time across the CP collection, the trend indicator is considered to be indicative of ventricular remodeling and a positive response to therapy. Alternatively, when the select AT difference increases over time across the CP collection, the trend indicator is considered to be indicative of a worsening in a HF status. Similarly, when the select difference remains constant across the CP collection, the trend indicator is considered to indicate no change in a HF status.

The foregoing example is described in connection with utilizing a maximum difference in the activation times, however it is understood that alternative mathematical relations between the activation times may be analyzed. For example, the processors may determine a standard deviation over the activation times from RV to each of the four LV sensing sites across the CP collection. The standard deviation is expected to be smaller when dyssynchrony is reduced. As explained in connection with FIG. 3B, at 350-362, when the processors identify a decreasing trend in the standard deviation for the activation times across the CP collection, the trend indicator is considered to be indicative of ventricular remodeling and a positive response to therapy. Alternatively, when the processors identify an increasing trend in the standard deviation for the activation times across the CP collection, the trend indicator is considered to be indicative of a worsening in a HF status. Similarly, when the standard deviation remains constant across the CP collection, the trend indicator is considered to indicate no change in a HF status.

As another example, the activation time metric may correspond to a conduction non-uniformity in the LV. By way of example, conduction non-uniformity may be determined in connection with the process described in U.S. Pat. No. 9,675,805 titled "method and system for localizing left ventricular conduction non-uniformity", issuing Jun. 13, 2017, the complete subject matter of which is hereby expressly incorporated by reference in its entirety. As one example, the conduction non-uniformity in the LV may be quantified by dividing i) a maximum activation time difference for each pair of neighboring LV sensing sites by ii) a total difference in activation time among all 4 LV electrodes. For example, with reference to FIG. 4B, panel A, the processors may determine a conduction non-uniformity by determining a total difference 464 in activation time among the four LV sensing sites and determine the maximum AT difference for each pair of neighboring LV sensing sites (e.g., 461-463). In panel A, activation time 463 would correspond to the maximum activation time between a pair of neighboring LV sensing sites, and thus the activation time 463 would be divided by the total difference 464 to determine a conduction non-uniformity in connection with the conduction pattern associated with panel A. The processors repeat the determination of conduction non-uniformity in connection with each conduction panel in the CP collection.

A reduction in the conduction non-uniformity would be indicative of ventricular remodeling and a positive response to therapy. As explained in connection with FIG. 3B, at 350-362, when the processors identify a decreasing trend in the conduction non-uniformity across the CP collection, the trend indicator is considered to be indicative of ventricular remodeling and a positive response to therapy. Alternatively, when the processors identify an increasing trend in the conduction non-uniformity for the activation times across the CP collection, the trend indicator is considered to be indicative of a worsening in a HF status. Similarly, when the conduction non-uniformity remains constant across the CP collection, the trend indicator is considered to indicate no change in a patient's HF status.

As another example, the activation time metric may correspond to conduction velocity in the LV. The processors quantify the conduction velocity in the LV based on an assumed distance between each pairs of neighboring LV sensing sites and the activation time difference for the pairs of neighboring LV sensing sites. The processors may calculate conduction velocity in various manners, including the process described in U.S. Pat. No. 9,675,805, referenced above. Faster conduction velocities would indicate ventricular remodeling and a positive response to therapy. As explained in connection with FIG. 3B, at 350-362, when the processors identify an increasing decreasing trend in the conduction velocity across the CP collection, the trend indicator is considered to be indicative of ventricular remodeling and a positive response to therapy. Alternatively, when the processors identify a decreasing trend in the conduction velocity for the activation times across the CP collection, the trend indicator is considered to be indicative of a worsening in a HF status. Similarly, when the conduction velocity remains constant across the CP collection, the trend indicator is considered to indicate no change in a patient's HF status.

Additionally or alternatively, the processors may classify the fastest conduction pathway by the order of activation of the 5 electrodes (e.g., "RV→LVD1→LVM2→LVM3→LVP4"). A change in the order of activation indicates a change in the general direction of wave front propagation, which could be classified as either improvement or deterioration of the patient's HF status.

As yet another example, the activation time metric may correspond to chronotropic incompetence of the LV cardiac tissue linked to a patient heart failure condition. The IMD assess chronotropic incompetence by applying a ramped stimulation protocol. The processors assess a sequence and time of activation during a basic cycle length at each of the LV sensing sites and record the HF assessment as a baseline or starting point. Thereafter, the processors assess chronotropic incompetence by delivering a sequence of RV pacing pulses at increasing prematurity (relative to the basic cycle length). For example, the series of RV pacing pulses may be delivered 70%, 60%, 50%, 40%, etc. of the basic cycle length over time. The LV tissue should respond in a somewhat predictable manner when the patient's heart is experiencing positive remodeling, such as based on a priority information and/or prior behavior by the current patient. The predictable response should occur regardless of how premature the RV pacing pulse is delivered. When the LV tissue responds in the predictable manner in response to the premature RV pacing pulses, as explained in connection with FIG. 3B, at 350-362, the one or more processors may determine that the tissue is undergoing positive remodeling and is exhibiting restored chronotropic competence.

Figure 4F:
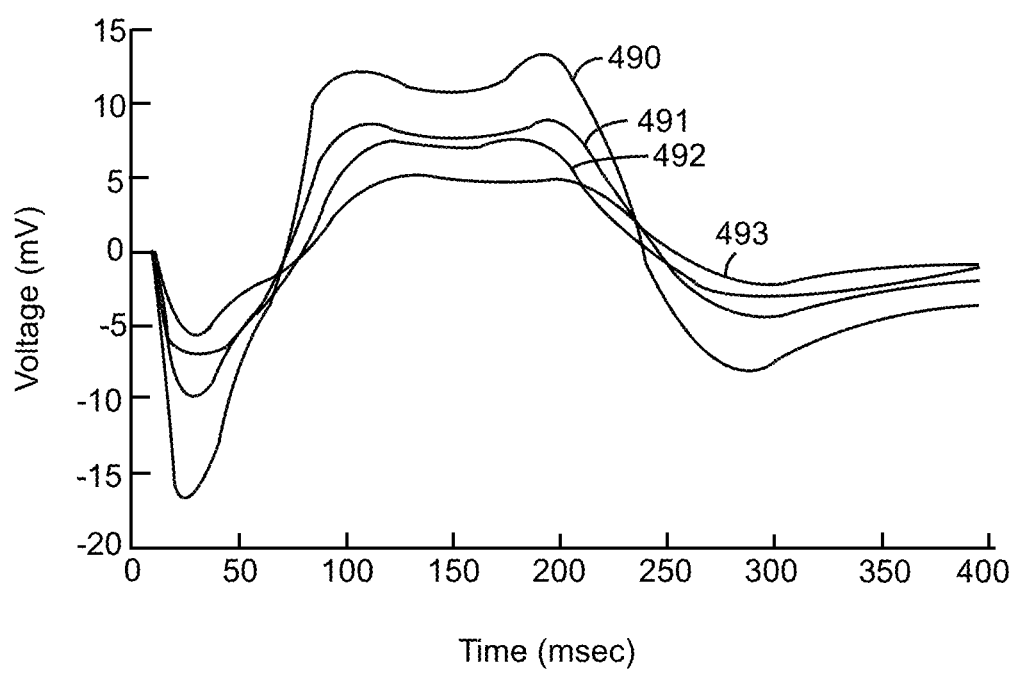
FIG. 4F illustrates graphs simulating electrocardiogram (EGM) morphologies for a collection of events that were recorded over time during HF induction in connection with rapid pacing by an IMD in accordance with embodiments herein.

At 324, the one or more processors apply a morphology metric to the morphology collection to calculate an MP trend indicator. In addition to activation patterns, which indicate the order in which the wave front passes each sensing site/electrode, individual EGM morphologies can also reflect electromechanical changes in the ventricles. EGMs capture more comprehensive information describing the propagating wave fronts as they move toward and away from each electrode. It has been shown that evoked responses sensed at LV sensing sites (in response to RV paced events) change in morphology in connection with a degradation or worsening of an HF condition or status. FIG. 4F illustrates graphs simulating EGM morphologies for a collection of events that were recorded over time during HF induction in connection with rapid pacing by an IMD. EGM morphology 490 corresponds to a baseline morphology, while EGM morphology 491 was collected while an IMD was delivering RV rapid pacing at a rate of approximately 190 bpm. EGM morphology 492 was collected while an IMD was delivering RV rapid pacing at a rate of approximately 210 bpm, while EGM morphology 493 was collected while an IMD was delivering RV rapid pacing at a rate of approximately 230 bpm. As shown in FIG. 4F the EGM morphologies 490-493 progressively drop in amplitude (both positive and negative) and lose other details within the shape thereby indicating a progressively worsening HF status.

At 324, the one or more processors apply one or more morphology metrics to the morphology collection, such as EGM morphologies 490-493. Morphology metrics may be characterized in various manners, with each morphology metric used to classify the HF disease status of a patient (i.e., improving vs. deteriorating). The MP metric comprises at least one of an electrical synchrony metric, electrically viable local tissue metric, pacing depolarization integral metric, slope based electrical excited ability metric or template matching score metric. Similar to activation time metrics associated with activation times, the EGM morphology-based metrics can be analyzed to determine HF based heart failure indicators that exhibit HF trends. When the HF trend exceeds one or more preset thresholds, the one or more processors may notify a clinician of a change in the trend, such as whether an HF status has worsened, become better or otherwise.

As an example, the morphology metric may correspond to electrical synchrony that may be determined from an EGM-based QRS duration, which represents a surrogate of a standard surface ECG QRS duration. The processors analyze the morphology collection and determine EGM-based QRS durations in connection with each morphology. By way of example, the one or more processors may implement the methods and systems described in U.S. patent application Ser. No. 16/752,839, filed 27 Jan. 2020 (now U.S. Pat. No. 11,123,006, issued 21 Sep. 2021) titled "Method and Device for Electrogram Based Estimation of QRS Duration", the complete subject matter of which is expressly incorporated herein by reference in its entirety. Thus, when the processors identify a trend indicator of interest (350-362 in FIG. 3B) (e.g., reducing trend) in the QRS duration over the collection of morphologies, the trend indicator is considered to be indicative of improvements an electrical resynchronization and a positive response to CRT therapy. Alternatively, when the processors identify an increasing trend indicator in the QRS duration over the collection of morphologies, the trend indicator is considered to be indicative of worsening electrical synchronization and a negative response to CRT therapy. Similarly, when the QRS duration remains constant across the morphology collection, the trend indicator is considered to indicate no change in a patient's HF status.

As another example, the morphology metric may correspond to whether a local LV tissue is electrically viable. To determine a trend indicator related to electrical viability of local tissue, the one or more processors determine a maximum amplitude of each morphology within the morphology collection. The maximum amplitude may be a positive or negative amplitude. The maximum amplitude quantifies an amount of electrical viability in myocardium in the local vicinity of the corresponding LV sensing site. The one or more processors identify, as the trend indicator of interest, the maximum EGM amplitude in connection with each morphology. When the processors identify an increasing trend or large EGM amplitude (e.g., 350-362 in FIG. 3B), the trend indicator is considered to be indicative of an improvement in electrical viability of the local LV tissue and a positive response to CRT therapy. Alternatively, when the processors identify a decreasing trend or relatively small EGM amplitude, the trend indicator is considered to be indicative of worsening electrical viability of the local LV tissue and eight negative response to CRT therapy. Similarly, when the EGM amplitude remains relatively unchanged, the trend indicator is considered to indicate no change in the patient's HF status.

As another example, the morphology metric may correspond to a Paced depolarization integral (PDI). In connection there with, the one or more processors may utilize a combination of the EGM QRS duration and amplitudes to apply an "area under the curve". Trends in the size of the paced depolarization integral represent a trend indicator of interest. When the processors identify an increasing trend in the PDI (e.g., 350-362 in FIG. 3B), the trend indicator is considered to be indicative of an improvement in the HF status and indicates a positive response to CRT therapy. Alternatively, when the processors identify a decreasing trend in the PDI, the trend indicator is considered to be indicative of a worsening HF status. When the PDI remains relatively unchanged, the trend indicator is considered to indicate no change in the patient's HF status.

As another example, the morphology metric may correspond to electrical excitability which may be quantified based on morphology slope trends, such as a maximum positive upward slope or minimum downward negative slow of the EGM morphology. The slope of the action potential for a local LV sensing site can be used to assess electrical excitability. The positive or negative slope of the EGM morphology is simply the combination of electrical activity of all of the myocytes in the vicinity of the EGM electrodes. Less viable myocardial tissue would yield smaller slope magnitudes. Accordingly, when the processors identify increasing trends in the slope magnitude (e.g., 350-362 in FIG. 3B), the trend indicator is considered to be indicative of an improvement in the electrical excitability of the myocardium. Alternatively, when the processors identify decreasing trends in the slope magnitude, the trend indicator is considered to be indicative of worsening in the electrical excitability of the myocardium. When the slope magnitude remains relatively unchanged over a morphology collection, the trend indicator is considered to indicate no change in the patient's HF status.

As another example, the morphology metric may correspond to a template matching score. The EGM morphology tends to return toward a standard shape, and away from an LBBB-type morphology, as the heart responds favorably to CRT therapy. The one or more processors may compare the morphologies within the morphology collection to one or more morphology templates, and determine one or more scores concerning a degree to which the individual morphologies match a morphology template. The morphology templates may represent known, normal EGM morphologies. Changes in the score represent a trend in a score indicator that affords a desirable feature to assess HF status. For example, a known, normal EGM morphology template could be obtained, and the one or more processors apply a cross-correlation coefficient (CC) of patient's LV EGM morphology to the known, normal EGM morphology template. Positive trending in the cross correlation would indicate patients responding favorably to CRT. Thus, when the processors identify positive trends in the cross correlation (e.g., 350-362 in FIG. 3B), the trend indicator is considered to be indicative of an improvement in the patient's HF status. Alternatively, when the processors identify negative trends of the cross correlation, the trend indicator is considered to be indicative of a worsening in the patient's HF status. When the cross correlation trend remains relatively unchanged, the trend indicator is considered to indicate no change in the patient's HF status.

At 326, the one or more processors determine whether to repeat the application of the morphology metric in connection with inter-electrode differences between morphologies associated with different LV sensing sites. If so, flow returns to 324 and the morphology metric is applied to inter-electrode differences between the morphologies to calculate and inter-electrode MP trend indicator. For example, the microcontroller 160 and/or CPU 602 may identify adjacent electrode combinations available at the LV lead 124. For example, when the LV lead 124 includes the electrodes D1, M2, M3 and P4, the adjacent electrode combinations would include D1+M2, M2+M3 and M3+P4. As noted herein, an adjacent electrode combination may include more than two electrodes that are arranged successive with one another. For example, an adjacent electrode combination may represent D1+M2+M3, M2+M3+P4, and the like. Each adjacent electrode combination represents adjacent LV sensing sites for which the process may determine whether the local tissue exhibits heterogeneity electrical behavior or dyssynchrony.

The process described above in connection with FIG. 3A applies activation time metrics and morphology metrics to morphologies and conduction patterns measured at individual LV sensing sites/LV electrode. Additionally or alternatively, the AT metric and morphology metrics may be applied to ensembles (e.g., mean, average or other statistical combinations) of morphologies and conduction patterns from some or all RV and LV electrodes. The foregoing AT and morphology metrics are expected to calculate CP based and MP based trend indicators that change as the ventricles respond to CRT. It is also possible that differences in the EGM morphology metrics between neighboring electrodes may slowly diminish as wave fronts propagate across the LV sensing sites more evenly. Therefore, the processors may apply the morphology metrics (based on the decision at 326) to inter-electrode differences in connection with assessing HF progression and tracking the inter-electrode differences over time.

When the processors determine to not repeat the morphology metric in connection with inter-electrode differences (or the morphology metric has already been applied to inter-electrode differences), flow continues to 328.

At 328, the one or more processors store the CP trend indicators and MP trend indicators along with timestamps indicating the point in time or time interval for which the HF indicators correspond. Thereafter, flow continues to FIG. 3B, as explained herein, the CP based and MP based trend indicators are used to calculate HF trends and such trends are used to classify an HF status (also referred to as a patient condition).

FIG. 3B illustrates a process for classifying a patient condition based on trend indicators to form an HF assessment and to provide notifications of the HF assessment in accordance with embodiments herein. The operations of FIG. 3B may be performed by one or more processors of an implantable medical device, a local external device and/or a remote server. By way of example, the process of FIG. 3B may represent a device-based method to establish long-term trends in ventricular reverse remodeling as patients respond to CRT over time, independent of occasional in-clinic echocardiography or ECG measurements. Daily averages of LV electrode activation patterns and/or EGM morphologies (e.g., EGM waveforms, EGM duration, QRS duration) can be saved and transmitted to a remote server. Clinicians may access records on the server and/or the server may push notifications to clinicians to enable clinicians to view long-term trends as they develop.

Embodiments herein provide more than simply displaying combinations of the aforementioned metrics, as the mere display of raw data provides limited treatment information to clinicians. Instead, embodiments herein provide a method and system in which (1) the IMD collects activation times and EGMs at discrete intervals (e.g., hourly, daily, weekly), (2) the IMD transmits the data to a local external device and/or remote server, (3) the IMD, local external device and/or remote server apply the morphology and AT metrics, (4) the IMD, local external device and/or remote server classify the patient's current response to HF therapy (e.g., improved, deteriorated, no change), and (5) the IMD, local external device and/or remote server notify the clinician (if the clinician desires to receive a notification) if a patient's HF status changes. Embodiments herein enable programmable thresholds to be set in connection with classifying a patient's HF response/status. For example, if the EGM QRS duration is elevated by more than 5% (relative to baseline) for 7 consecutive days, an email can be sent to the clinician with a summary of the QRS duration history and a recommendation for an in-clinic follow-up assessment. Various HF trending parameters extracted from RV-LV conduction delays and EGM morphologies can be also combined as one HF index or a composite score based on X out of Y parameters crossing respective thresholds. Accordingly, the physician is provided with one single index that describes the overall HF status based on conduction and morphology. Additionally or alternatively, physicians can choose boundaries for alerts based on their standard of practice.

The description above describes the monitoring of activation patterns and EGM morphologies during intrinsic conduction (either A-paced or A-sensed with intrinsic conduction to the RV and LV electrodes). However, the activation patterns and EGM morphologies can also be tracked in parallel for other stimulus origins, including RV-paced and LV-paced at each of the 4 electrodes.

At 350, the one or more processors obtain and compare one or more CP based trend indicators with one or more thresholds. At 352, the one or more processors obtain and compare one or more MP based trend indicators with one or more thresholds. At 354, the one or more processors determine whether the CP and MP trend indicators satisfy positive thresholds. When the trend indicators satisfy one or more positive thresholds, flow moves to 356. When the trend indicators do not satisfy positive thresholds, flow moves to 358. At 358, the one or more processors determine whether the CP and MP trend indicators satisfy negative thresholds. When the trend indicators satisfy negative thresholds, flow moves to 360. When the trend indicators do not satisfy negative thresholds, flow moves to 362.

Returning to 354, when flow advances to 356, at 356 the one or more processors classify the patient condition as "improving" for an HF assessment. Alternatively, when flow progresses to 360, the one or more processors classify the patient condition as "worsening" for the HF assessment. When the trend indicators do not indicate either of an improving or worsening HF assessment, flow moves from 354 to 358 to 362. At 362, the one or more processors classify the patient condition as "no change" for the HF assessment.

Next, the operations at 350-362 are described in connection with one or more particular trend indicators. As noted above in connection with FIG. 3B, the CP-based trend indicator may be in connection with at least one of a dyssynchrony metric, conduction nonuniformity metric, conduction velocity metric, fastest conduction pathway metric or chronotropic incompetence metric, with one or more thresholds. The MP-based trend indicator may be in connection with at least one of an electrical synchrony metric, electrically viable local tissue metric, pacing depolarization integral metric, slope based electrical excited ability metric or template matching score metric. The thresholds may be positive or negative in that, when the trend indicator satisfies a positive threshold, the HF assessment is set to positive (e.g., the patient's condition is improving). Alternatively, when the trend indicator satisfies a negative threshold, the HF assessment is set to negative (e.g., the patient's condition is worsening). When the trend indicator does not satisfy the threshold, the HF assessment is set to "no change".

By way of example only, when the AT metric corresponds to general dyssynchrony, a positive threshold may be set at 354 such that when a maximum difference in activation times among the sensing sites falls below a difference threshold, the positive threshold would be determined to be satisfied and flow would move to 356, depending upon other metrics considered. At 356, the patient condition would be classified as improving. Additionally or alternatively, when the AT metric corresponds to conduction velocity, a positive threshold may be set at 354 such that when the conduction velocity exceeds a velocity threshold, the positive threshold would be determined to be satisfied and flow would move to 356. As MP metric based examples, when the MP based metric corresponds to electrical synchrony, a QRS duration threshold may be defined. At 354, when the MP trend indicator for the QRS duration falls below the QRS duration threshold, this would be interpreted as satisfying a positive threshold at 354 and flow would advanced the 356, depending upon other metrics considered.

Alternatively, at 354, when a maximum difference in activation times exceeds the difference threshold, the positive threshold would not be satisfied and flow would move to 358. At 358, the maximum difference in activation times is compared to a negative threshold (e.g., a negative difference threshold that is higher than the positive difference threshold). When the maximum difference exceeds the higher negative difference threshold, the negative threshold would be satisfied and flow would move to 360 where the HF assessment is set to indicate that the patient condition is worsening. Alternatively, when the maximum difference falls between the lower positive threshold and higher negative threshold, flow would navigate to 362 where the HF assessment would be set to a no change assessment.

It is recognized that one or more combinations of the CP-based trend indicators and MP-based trend indicators may be compared to corresponding positive and negative thresholds at 354 and 358 to determine the HF assessment. Additionally or alternatively, the operations at 354 and 358 may apply a weighted combinations of the comparisons of the trend indicators to positive and negative thresholds. For example, when an individual CP-based trend indicator is compared to a corresponding positive threshold, a score may be applied indicative of how close the trend indicator is to a threshold. The comparisons and scores may be combined for multiple trend indicators. When the cumulative comparison is sufficient, flow may advance to 356. Alternatively, when the multiple trend indicators do not score high enough, flow moves to 358. At 358, trend indicators for multiple CP and MP-based trends may be combined in a similar manner. Additionally or alternatively, the operations at 354 through 358 may be combined into a single threshold comparison.

Following the classification of patient condition as a corresponding type of HF assessment, flow moves to 364. At 364, the one or more processors determine whether an HF assessment notification should be conveyed to one or more individuals. When the processors determined to not send an HF assessment notification, the process of FIG. 3B ends. Alternatively, when the processors determined to send an HF assessment notification, flow continues to 364.

At 366, the one or more processors prepare an HF assessment notification. For example, the HF assessment notification may include the CP trend trends, the MP trend trends, the classification of the patient condition, as well as other information in connection there with. The HF assessment notification is conveyed to one or more designated destination devices. For example, the HF assessment notification may be sent to an electronic account (e.g., email, SMS text) of a physician caring for an individual. The HF assessment notification may be sent to a central clearinghouse where a group of individuals monitor and further process the HF assessment notifications. Additionally or alternatively, the HF assessment notification may be sent to one or more devices within a medical network (e.g., workstations, smart phones, tablet devices, laptop computers and the like) for one or more physicians caring for an individual.

Figure 5:
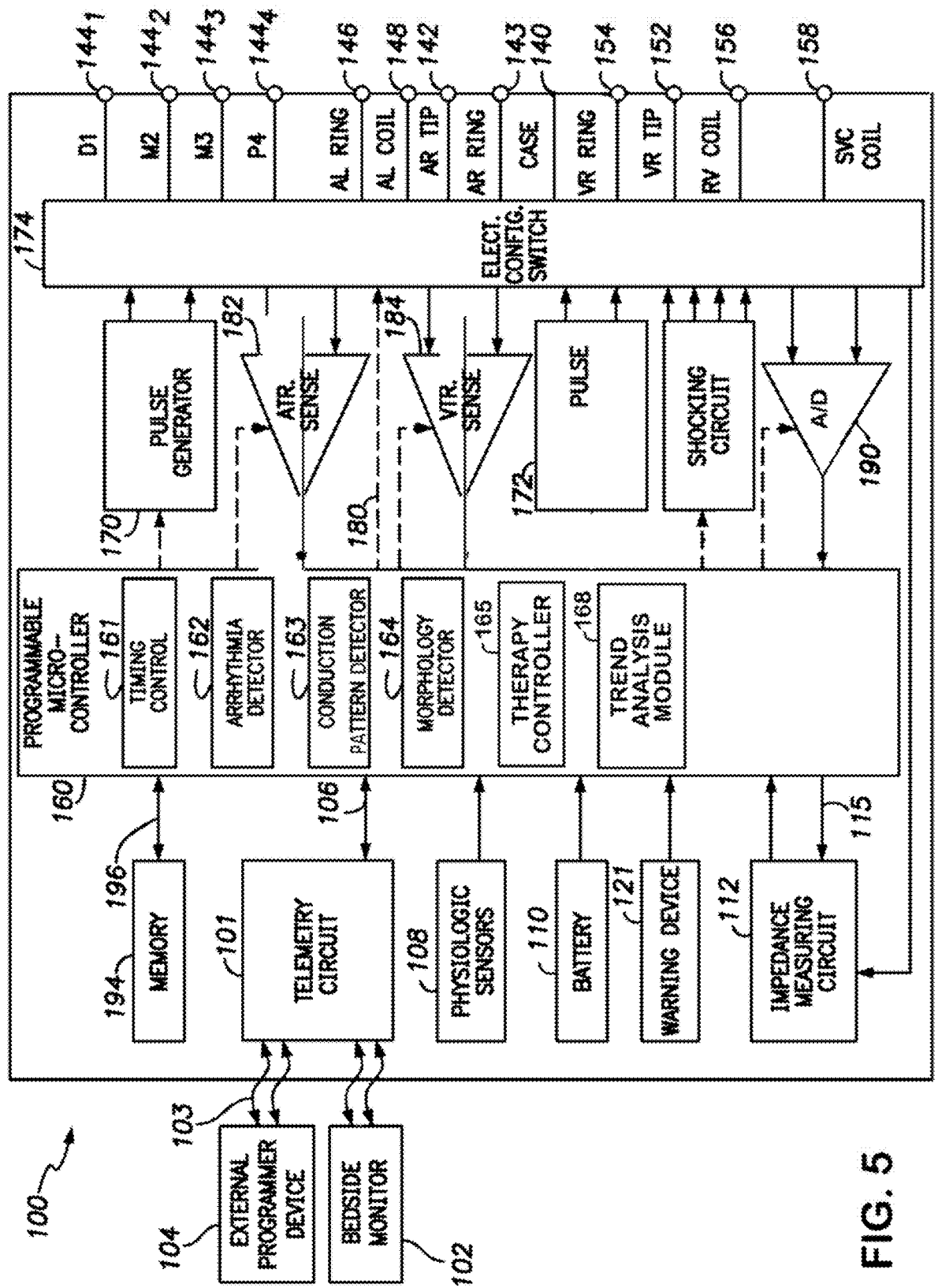
FIG. 5 illustrates a simplified block diagram of internal components of the IMD (e.g., IMD) according to an embodiment.

FIG. 5 illustrates a simplified block diagram of internal components of the IMD 100 (e.g., IMD) according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 140 for IMD 100 may be programmably selected to act as the anode for at least some unipolar modes. The CAN 140 may further be used as a return electrode alone or in combination with one or more of the coil electrodes 128, 136, and 138 (all shown in FIG. 1) for shocking purposes.

The IMD 100 further includes a connector (not shown) having a plurality of terminals, 142, 143, $144_1$-$144_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal (AR TIP) 142 adapted for connection to the atrial tip electrode 122 (shown in FIG. 1) and an RA ring (AR RING) electrode 143 adapted for connection to the RA ring electrode 123 (shown in FIG. 1). To achieve left chamber sensing, pacing, and shocking, the connector includes an LV tip terminal $144_1$ adapted for connection to the D1 electrode and additional LV electrode terminals $144_2$, $144_3$, and $144_4$ adapted for connection to the M2, M3, and P4 electrodes, respectively, of the quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV coil terminal (RV COIL) 156, and an SVC coil terminal (SVC COIL) 158, which are adapted for connection to the RV tip electrode 132, the RV ring electrode 134, the RV coil electrode 136, and the SVC coil electrode 138 (all four electrodes shown in FIG. 1), respectively.

The IMD 100 includes a programmable microcontroller 160 (also referred to herein as a control unit or controller) that includes a microprocessor or equivalent control circuitry, designed specifically for controlling the delivery of stimulation therapy. The microcontroller 160 may further include RAM or ROM memory, logic and timing circuitry, state machine circuitry, and/or I/O circuitry. The microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes.

A pulse generator 170 and a pulse generator 172 are configured to generate and deliver a pacing pulse from at least one RV or RA pacing site, such as at one or more pacing sites along the RA lead 120, the RV lead 130, and/or the LV lead 124 (all three leads shown in FIG. 1). The pulse generators 170, 172 are controlled by the microcontroller 160 via appropriate control signals to trigger or inhibit the stimulation pulses, including the timing and output of the pulses. The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, controls the polarity of the stimulation pulses (e.g., unipolar, bipolar, combipolar, etc.) by selectively actuating the appropriate combination of switches (not shown) as is known in the art. The switch 174 also switches among the various LV electrodes 126 to select the channels (e.g., vectors) to deliver and/or sense one or more of the pacing pulses. As explained herein, the switch 174 couples multiple LV electrode terminals $144_1$-$144_4$ correspond to cathodes when connected to the pulse generator 172.

Atrial sensors or sensing circuits 182 and ventricular sensors or sensing circuits 184 may also be selectively coupled to the RA lead 120, the LV lead 124, and/or the RV lead 130 (all three leads shown in FIG. 1) through the switch 174. The atrial and ventricular sensors 182 and 184 have the ability to detect the presence of cardiac activity in each of the four chambers of the heart 105 (shown in FIG. 1). For example, the ventricular sensor 184 is configured to sense LV activation events at multiple LV sensing sites, where the activation events are generated in response to a pacing pulse or an intrinsic event. In an embodiment, the ventricular sensor 184 senses along at least four sensing vectors, each sensing vector utilizing a sensing electrode in the left ventricle.

The atrial sensing circuits 182 and ventricular sensing circuits 184 may include dedicated sense amplifiers, multiplexed amplifiers, or shared amplifiers. The switch 174 determines the "sensing polarity" or sensing vector of the cardiac signal by selectively opening and/or closing the appropriate switches, as is known in the art. In this way, a clinician may program the sensing polarity independent of the stimulation polarity.

Cardiac signals are also applied to the inputs of an analog-to-digital (A/D) data acquisition system 190. The A/D data acquisition system 190 is configured to acquire intracardiac electrogram (EGM) signals, convert the raw analog data into a digital signal, and store the digital signals for later processing and/or telemetric transmission. The telemetric transmission may be to an external programmer device 104, a bedside monitor, and/or a personal advisory module (PAM) 102. The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control module 161 to control the timing of the stimulation pacing pulses, including, but not limited to, pacing rate, atrio-ventricular delay, interatrial conduction delay, interventricular conduction delay, and/or intraventricular delay. The timing control module 161 can also keep track of the timing of refractory periods, blanking intervals, noise detection windows, evoked response detection windows, alert intervals, marker channel timing, etc., which is known in the art.

The microcontroller 160 further includes an arrhythmia detector 162 for operating the system 100 as an implantable cardioverter/defibrillator device. The detector 162 determines desirable times to administer various therapies. For example, the detector 162 may detect the occurrence of an arrhythmia and automatically control the application of an appropriate electrical shock therapy to the heart aimed at terminating the detected arrhythmia.

The microcontroller 160 includes a therapy controller 165 to manage pacing therapy, which can be performed in conjunction with CRT pacing. As an example, the therapy controller 165 may control the pulse generator 172 to simultaneously deliver a pacing pulse over a select pacing vector. The arrhythmia detector 162, morphology detector 164, and/or therapy controller 165 may be implemented in hardware as part of the microcontroller 160, or as software/firmware instructions programmed into the system and executed on the microcontroller 160 during certain modes of operation. The therapy controller 165 also controls delivery of CRT pacing pulses to synchronize the contractions of the right and left ventricles. The therapy controller 165 controls the number, timing, and output of the CRT pacing pulses delivered during each cardiac cycle, as well as over which pacing vectors the pacing pulses are to be delivered.

The microcontroller 160 may additionally include a morphology detector 164, a conduction pattern detector 163, and a trend analysis module 168 that perform the operations described herein in connection with FIGS. 1-4F. The morphology detector 164 determines morphologies for cardiac signals sensed at the LV activation sites and associated with LV activation events. The conduction pattern detector 163 determines conduction patterns across the LV sensing sites based on LV activation events. The trend analysis module 168 may implement the operations described in connection with FIGS. 3A and 3B, such as to calculate an HF trend based on the CP collection and the MP collection and classifies a patient condition based on the HF trend to form an HF assessment. Among other things, the trend analysis module 168 calculates a CP-based trend indicator by applying an AT metric to the CP collection; and calculates an MP-based trend indicator by applying an MP metric to the MP collection. The trend analysis module 168 applying, as the AT metric, at least one of a dyssynchrony metric, conduction nonuniformity metric, conduction velocity metric, fastest conduction pathway metric or chronotropic incompetence metric. The trend analysis module 168 applies, as the MP metric, at least one of an electrical synchrony metric, electrically viable local tissue metric, pacing depolarization integral metric, slope based electrical excited ability metric or template matching score metric.

The microcontroller 160 is further coupled to a memory 194 by a suitable data/address bus 196. The programmable operating parameters used by the microcontroller 160 are stored in the memory 194 and modified, as required, in order to customize the operation of IMD 100 to suit the needs of a particular patient. Such operating parameters define, for example, the amplitude or magnitude of the generated pacing pulses, wave shape, pulse duration, and/or vector (e.g., including electrode polarity) for the pacing pulses. Other pacing parameters may include base rate, rest rate, and/or circadian base rate. The memory 194 also stores conduction patterns or morphologies, CP collections, MP collections, CP-based trend indicators, MP-based trend indicators, HF trends, AT metrics, MP metrics as well as other data and information described herein.

Optionally, the operating parameters of the implantable IMD 100 may be non-invasively programmed into the memory 194 through a telemetry circuit 101 in telemetric communication with an external programmer device 104 or a bedside monitor 102, such as a programmer, trans-telephonic transceiver, or a diagnostic system analyzer. The telemetry circuit 101 is activated by the microcontroller 160 through a control signal 106. The telemetry circuit 101 may allow IEGMs, conduction patterns, morphologies, CP collections, MP collections, CP-based trend indicators, MP-based trend indicators, HF trends, AT metrics, MP metrics as well as other data and information described herein, and status information relating to the operation of IMD 100 (contained in the microcontroller 160 or the memory 194) to be sent to the external programmer device 104 and/or bedside monitor 102, and vice-versa, through an established communication link 103. An internal warning device 121 may be provided for generating perceptible warning signals to a patient and/or caregiver via vibration, voltage, or other methods.

IMD 100 further includes an accelerometer or other physiologic sensor 108. The physiologic sensor 108 is commonly referred to as a "rate-responsive" sensor because it may be used to adjust the pacing stimulation rate according to the exercise state (e.g., heart rate) of the patient. However, the physiological sensor 108 may further be used to detect changes in cardiac output, changes in the physiological condition of the heart, and/or diurnal changes in activity (e.g., detecting sleep and wake states and arousal from sleep).

The IMD 100 additionally includes a battery 110, which provides operating power to all of the circuits therein. The makeup of the battery 110 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 110 may also be configured to have a predictable discharge characteristic so that elective replacement time can be detected.

Optionally, the IMD 100 includes an impedance measuring circuit 112, which is enabled by the microcontroller 160 via a control signal 115. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is coupled to the switch 174 so that any desired electrode may be used.

The above described implantable medical device 100 was described as an exemplary IMD. One of ordinary skill in the art would understand that one or more embodiments herein may be used with alternative types of implantable devices. Accordingly, embodiments should not be limited to using only the above described device 100.

Figure 6:
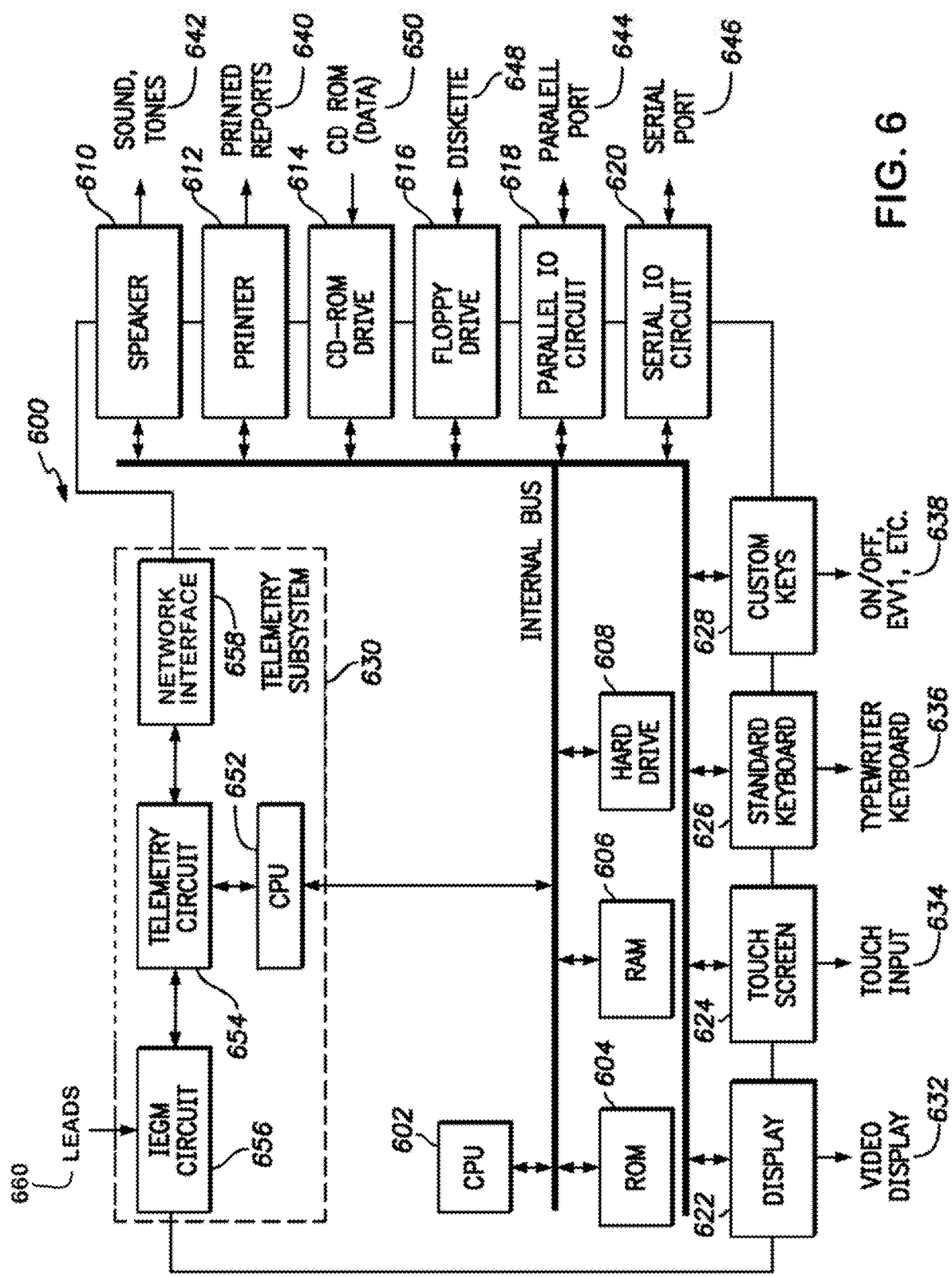
FIG. 6 illustrates a functional block diagram of an external device that is operated in accordance with embodiments herein.

FIG. 6 illustrates a functional block diagram of an external device 600 that is operated in accordance with the processes described herein and to interface with the implantable medical device 100 as shown in FIGS. 1 and 2 and described herein. The external device 600 may be a local external device, an external programmer device and the like. The external device 600 may take the form of a workstation, a portable computer, an IMD programmer, a tablet device, a laptop computer, a smart phone, a PDA, and the like. The external device 600 includes an internal bus that connects/interfaces with a Central Processing Unit (CPU) 602, ROM 604, RAM 606, a hard drive 608, a speaker 610, a printer 612, a CD-ROM drive 614, a floppy drive 616, a parallel I/O circuit 618, a serial I/O circuit 620, a display 622, a touch screen 624, a standard keyboard 626, custom keys 628, and/or a telemetry subsystem 630. The internal bus is an address/data bus that transfers information between the various components described herein. The hard drive 608 may store operational programs as well as data, such as waveform templates, determinations on presence of PNS at various electrode locations, and/or capture thresholds for pacing vectors.

The CPU 602 includes a microprocessor, a micro-controller, and/or equivalent control circuitry, designed specifically to control interfacing with the external device 600 and with the IMD 100. The CPU 602 may include RAM or ROM memory, logic and timing circuitry, state machine circuitry, and/or I/O circuitry to interface with the IMD 100. The ROM 604, RAM 606 and/or hard drive 608 store program instructions that one executed by one or more processors (e.g., the CPU 602) to perform all or a portion of the operations described herein in connection with FIGS. 3A-3B.

The display 622 may be connected to a video display 632. The display 622 displays various forms of information related to the processes described herein. The touch screen 624 may display graphic user information relating to the IMD 100. The touch screen 624 accepts a user's touch input 634 when selections are made. The keyboard 626 (e.g., a typewriter keyboard 636) allows a user to enter data to displayed fields, as well as interface with the telemetry subsystem 630. Furthermore, custom keys 628 turn on/off 638 (e.g., EWI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a flash memory stick. The CD-ROM drive 614 accepts CD ROMs 650. The CD-ROM drive 614 optionally may include a DVD port capable of reading and/or writing DVDs. Optionally one or more of the peripheral circuits/components at 610-620 may be omitted.

The telemetry subsystem 630 includes a central processing unit (CPU) 652 in electrical communication with a telemetry circuit 654, which communicates with both an IEGM circuit 656 and a network interface 658. The IEGM circuit 656 may be connected to leads 660. The IEGM circuit 656 is also connected to the implantable leads 120, 124 and 130 (shown in FIG. 1) to receive and process IEGM cardiac signals. Optionally, the IEGM cardiac signals sensed by the leads 120, 124 and 130 may be collected by the IMD 100 and then wirelessly transmitted to the telemetry subsystem 630 input of the external device 600. Optionally, the IEGM circuit 656 AB omitted entirely, such as in smart phones and standard commercially available laptop computers, tablet devices and the like.

The telemetry circuit 654 is configured to wirelessly communicate with the IMD 100. The network interface 658 is configured to communicate over a wired or wireless network, such as with a remote server. The external device 600 may wirelessly communicate with the IMD 100 and utilize protocols, such as Bluetooth, GSM, infrared wireless LANs, HIPERLAN, 3G, 4G, satellite, as well as circuit and packet data protocols, and the like. Alternatively, a hard-wired connection may be used to connect the external device 600 to the IMD 100.

Figure 7:
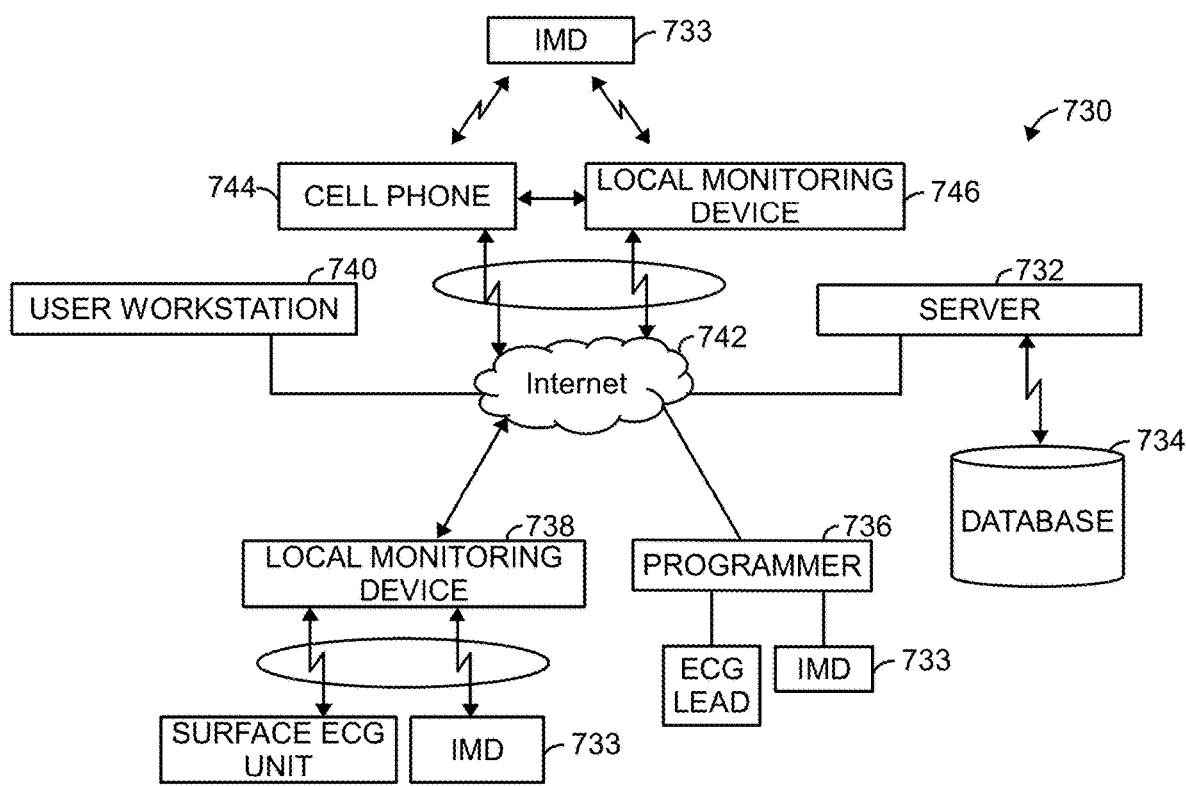
FIG. 7 illustrates a system in accordance with embodiments herein.

FIG. 7 illustrates a system 730 in accordance with embodiments herein. The system 730 includes a server 732 connected to a database 734, IMDs 733, a programmer 736, a local monitoring device 738 and a user workstation 740 electrically connected to a network 742. Any of the processor-based components in FIG. 7 (e.g., workstation 740, IMD 733, cell phone 744, local monitoring device 746, server 732, programmer 736) may perform the processes discussed herein. For example, the IMD 733 may perform the collection of conduction patterns and morphologies. The IMD 733, cell phone 744, local monitoring device 746, programmer 736, workstation 740 and/or server 732 may perform the calculation of the CP-based and MP-based trend indicators and/or the classification of the patent condition and transmission of the notification of the HF assessment.

The network 742 may provide cloud-based services over the internet, a voice over IP (VoIP) gateway, a local plain old telephone service (POTS), a public switched telephone network (PSTN), a cellular phone based network, and the like. Alternatively, the communication system 742 may be a local area network (LAN), a medical campus area network (CAN), a metropolitan area network (MAN), or a wide area network (WAM). The communication system 742 serves to provide a network that facilitates the transfer/receipt of data and other information between local and remote devices (relative to a patient). The server 732 is a computer system that provides services to the other computing devices on the network 742. The server 732 controls the communication of information such as conduction patterns or morphologies, CP collections, MP collections, CP-based trend indicators, MP-based trend indicators, HF trends, AT metrics, MP metrics as well as other data and information described herein, as well as cardiac activity data, bradycardia episode information, asystole episode information, AF episode information, markers, cardiac signal waveforms, ventricular and atrial heart rates, and detection thresholds. The server 732 interfaces with the network 742 to transfer information (e.g., conduction patterns or morphologies, CP collections, MP collections, CP-based trend indicators, MP-based trend indicators, HF trends, AT metrics, MP metrics as well as other data and information described herein) between the programmer 736, local monitoring devices 738, 746, user workstation 740, cell phone 744 and database 734. The database 734 stores information such as conduction patterns or morphologies, CP collections, MP collections, CP-based trend indicators, MP-based trend indicators, HF trends, AT metrics, MP metrics as well as other data and information described herein, as well as cardiac activity data, AF episode information, AF statistics, diagnostics, markers, cardiac signal waveforms, ventricular and atrial heart rates, detection thresholds, and the like, for a patient population. The information is downloaded into the database 734 via the server 732 or, alternatively, the information is uploaded to the server 732 from the database 734. The programmer 736 may reside in a patient's home, a hospital, or a physician's office. The programmer 736 interfaces with (e.g., in connection with a pacemaker) the IMD 733. The programmer 736 may wirelessly communicate with the IMD 733 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 736 to the IMD 733. The programmer 736 is able to acquire ECG from surface electrodes on a person (e.g., ECGs), electrograms (e.g., EGM) signals from the IMD 733, and/or cardiac activity data, AF episode information, AF statistics, diagnostics, markers, cardiac signal waveforms, ventricular and atrial heart rates, sensing parameter settings and detection thresholds from the IMD 733. The programmer 736 interfaces with the network 742, either via the internet, to upload the information acquired from the surface ECG unit 720, or the IMD 733, to the server 732.

The local monitoring device 738 interfaces with the communication system 742 to upload to the server 732 one or more of conduction patterns or morphologies, CP collections, MP collections, CP-based trend indicators, MP-based trend indicators, HF trends, AT metrics, MP metrics as well as other data and information described herein, as well as cardiac activity data set, AF episode information, AF statistics, diagnostics, markers, cardiac signal waveforms, ventricular and atrial heart rates, sensing parameter settings and detection thresholds. In one embodiment, the surface ECG unit 720 and the IMD 733 have a bi-directional connection with the local RF monitoring device 738 via a wireless connection. The local monitoring device 738 is able to acquire conduction patterns or morphologies, CP collections, MP collections, CP-based trend indicators, MP-based trend indicators, HF trends, AT metrics, MP metrics as well as other data and information described herein, from the IMD 733, and/or cardiac signal waveforms, ventricular and atrial heart rates, and detection thresholds from the IMD 733.

The user workstation 740 may be utilized by a physician or medical personnel to interface with the network 742 to download conduction patterns or morphologies, CP collections, MP collections, CP-based trend indicators, MP-based trend indicators, HF trends, AT metrics, MP metrics as well as other data and information described herein herein from the database 734, from the local monitoring devices 738, 746, from the IMD 733 or otherwise. Once downloaded, the user workstation 740 may process the data in accordance with one or more of the operations described above. The user workstation 740 may upload/push settings (e.g., sensing parameter settings), IMD instructions, other information and notifications to the cell phone 744, local monitoring devices 738, programmer 736, server 732 and/or IMD 733. For example, the user workstation 740 may provide instructions to the IMD 733 in order to update sensing parameter settings when the IMD 733 declares too many false AF detections.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method for monitoring a trend in heart failure (HF) progression, the method comprising:
    sensing ventricular activation events at multiple ventricular sensing sites, where the activation events are generated in response to an intrinsic or paced ventricular event;
    implementing program instructions on one or more processors for automatically:
        determining a conduction pattern (CP) across the sensing sites based on the activation events; repeating the sensing and determining operations, at select intervals, to build a CP collection; and
        calculating an HF trend based on the CP collection.

2. The method of claim 1, further comprising classifying a patient condition based on the HF trend to form an HF assessment.

3. The method of claim 1, wherein the performing further comprises: identifying a morphology pattern (MP) for cardiac signals associated with the activation events, the repeating builds an MP collection and the calculating calculates the HF trend based on the CP collection and the MP collection.

4. The method of claim 1, wherein the sensing sites are left ventricular sensing sites and the sensing comprises sensing left ventricular (LV) activation events at the multiple LV sensing sites.

5. The method of claim 1, wherein the calculating the HF trend comprises calculating a CP-based trend indicator and a morphology pattern (MP)-based trend indicator, and the method further comprising comparing the CP-based and MP-based trend indicators to corresponding thresholds to classify the patient condition as one of improved, deteriorated or no change.

6. The method of claim 1, wherein the sensing and determining operations are performed by an implantable medical device, while at least a portion of the calculating operation is performed by at least one of an external device and a remote server.

7. The method of claim 1, wherein the sensing, determining and classifying operations are performed by an implantable medical device, the method further comprising transmitting the HF trend from the implantable medical device to at least one of an external device and a remote server.

8. A method comprising:
    implementing program instructions on one or more processors for automatically:
    obtaining a conduction pattern (CP) collection of conduction patterns across multiple ventricular sensing sites; and
    calculating an HF trend based on the CP collection.

9. The method of claim 8, further comprising classifying a patient condition based on the HF trend to form an HF assessment.

10. The method of claim 8, wherein the method is a computer implemented method for monitoring a trend in heart failure (HF) progression in connection with left ventricular (LV) activation events sensed, over a select interval, at multiple LV sensing sites along a multi-electrode LV lead, where the activation events are generated in response to an intrinsic or paced ventricular event.

11. The method of claim 8, further comprising identifying a morphology pattern (MP) for cardiac signals associated with activation events, and repeating the identifying to obtain an MP collection, the calculating including calculating the HF trend based on the MP collection and the CP collection.

12. The method of claim 8, wherein the obtaining obtains the CP collection and a morphology pattern (MP) collection, and the calculating calculates the HF trend based on both of the CP collection and the MP collection.

13. The method of claim 8, wherein the obtaining the CP collection comprises at least one of i) accessing memory of an external device or remote server that stores the the CP collection, ii) receiving the the CP collection over a wireless communications link between an implantable medical device and a local external device, or iii) receiving the CP collection at a remote server over a network connection.

14. A system, comprising:
 electrodes configured to sense ventricular activation events at multiple sensing sites, where the activation events are to be generated in response to an intrinsic or paced ventricular event;
 memory to store program instructions, and one or more processors that, when executing the program instructions, are configured to automatically:
  determine a conduction pattern (CP) across the sensing sites based on the activation events;
  repeat the sensing and determining operations, at select intervals, to build a CP collection; and
  calculate an HF trend based on the CP collection.

15. The system of claim 14, wherein the one or more processors are configured to classify a patient condition based on the HF trend to form an HF assessment.

16. The system of claim 14, wherein the one or more processors are configured to identify a morphology pattern (MP) for cardiac signals associated with the activation events, repeat the identify operation to build an MP collection and calculate the HF trend based on the CP collection and the MP collection.

17. The system of claim 14, further comprising an implantable medical device (IMD) coupled to a multi-electrode LV lead, and a local external device configured to wirelessly communicate with the IMD, the local external device configured to communicate over a network with a remote server, the one or more processors comprising at least a first processor housed within the IMD and configured to perform the determining operation.

18. A system, comprising:
 electrodes configured to sense ventricular activation events at multiple sensing sites, where the activation events are to be generated in response to an intrinsic or paced ventricular event;
 memory to store program instructions, and one or more processors that, when executing the program instructions, are configured to automatically:
  obtain a conduction pattern (CP) collection of conduction patterns across multiple ventricular sensing sites; and
  calculate an HF trend based on the CP collection.

19. The system of claim 18, wherein the one or more processors are configured to classify a patient condition based on the HF trend to form an HF assessment.

20. The system of claim 18, wherein the one or more processors are further configured to obtain a morphology pattern (MP) collection and calculate the HF trend based on the MP collection and the CP collection.

* * * * *